United States Patent
O'Yang et al.

(10) Patent No.: US 7,307,082 B2
(45) Date of Patent: Dec. 11, 2007

(54) HETEROCYCLIC DERIVATIVES AS CRF ANTAGONISTS

(75) Inventors: Counde O'Yang, Sunnyvale, CA (US); Ryan Craig Schoenfeld, San Jose, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 393 days.

(21) Appl. No.: 10/839,323

(22) Filed: May 4, 2004

(65) Prior Publication Data

US 2004/0224964 A1    Nov. 11, 2004

Related U.S. Application Data

(60) Provisional application No. 60/468,878, filed on May 5, 2003.

(51) Int. Cl.
*A61P 25/00* (2006.01)
*A61K 31/519* (2006.01)
*C07D 487/04* (2006.01)

(52) U.S. Cl. .................. 514/265.1; 544/280
(58) Field of Classification Search ............. 514/265.1; 540/280
See application file for complete search history.

(56) References Cited

FOREIGN PATENT DOCUMENTS

| WO | WO98/01428 A1 | 1/1998 |
|---|---|---|
| WO | WO98/33798 A2 | 8/1998 |
| WO | WO 01/55148 A1 | 8/2001 |
| WO | WO 02/059083 A2 | 8/2002 |
| WO | WO 02/088095 A1 | 11/2002 |
| WO | WO 02/100863 A1 | 12/2002 |

OTHER PUBLICATIONS

Lanier, M. et al., "Small Molecule Corticotropin-Releasing Factor Antagonists," *Expert. Opin. Ther. Patents* 2002, 12 (11): 1619-1630.
Owens, M.J., et al., "Corticotropin-Releasing Factor Antagonists," *CNS Drugs* Aug. 1999 12(2): 85-92.

*Primary Examiner*—Brenda Coleman
(74) *Attorney, Agent, or Firm*—Brian L. Buckwalter

(57) ABSTRACT

This invention relates to compounds which are generally CRF-1 receptor antagonists and which are represented by Formula I wherein $X^1$ is $(CH_2)_n$ or CO, n is 0 to 2 and $R^1$, $R^2$, $R^3$ and $R^4$ are as defined in the specification; or individual isomers, racemic or non-racemic mixtures of isomers, or pharmaceutically acceptable salts thereof. The invention further relates to processes for preparing such compounds, to pharmaceutical compositions containing such compounds, and to methods for their use as therapeutic agents (I)

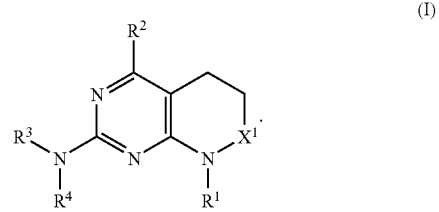

8 Claims, No Drawings

HETEROCYCLIC DERIVATIVES AS CRF ANTAGONISTS

CROSS REFERENCE TO PRIOR APPLICATION

This application claims benefit under Title 35 U.S.C. 119(e) of U.S. Provisional Application No. 60/468,878, filed May 5, 2003, which is hereby incorporated by reference in its entirety

FIELD OF THE INVENTION

This invention relates fused-pyrimidine derivatives with CRF activity, and associated pharmaceutical compositions, and methods for use as therapeutic agents.

BACKGROUND OF THE INVENTION

Corticotropin releasing factor (CRF) or hormone (CRH) is one of several neurohormones synthesized by specific hypothalamic nuclei in the brain where it activates the transcription of the pro-opiomelanocortin (POMC) gene resulting in release of adrenocorticotropic hormone (ACTH) and beta-endorphin from anterior pituitary cells (Vale et al, Science 213, 1394-1397 (1981)). The fundamental role of CRF is to prepare the organism for an appropriate response to various stressors such as physical trauma, insults of the immune system and social interactions. CRF also has CNS effects by acting at higher centers in the brain, particularly cortical regions where there is a widespread distribution of CRF neurons. CRF is believed to be a key intermediary in communication between the immune, central nervous, endocrine and cardiovascular systems (Sapolsky et al, Science 238, 522-524 (1987)). The role played by CRF in integrating the response of the immune system to physiological, psychological and immunological stressors has been described in the art, e.g. J. E. Blalock, Physiological Reviews 69, 1 (1989) and J. E. Morley, Life Sci. 41, 527 (1987).

CRF is a primary hormone controlling the hypothalamic-pituitary-adrenal axis. CRF exerts it pharmacological activity through at least two distinct G-protein coupled receptor subtypes which differ in their anatomical distribution and in their response to peptide ligands. Various splice modifications of these two subtypes have been observed (J. Saunders and J. P. Williams *New Developments in the Study of Corticotropin Releasing Factor, Ann. Rep. Med. Chem.* 2001 36:21-30). The first CRF receptor antagonists were peptides (see, e.g., Rivier et al., U.S. Pat. No. 4,605,642; Rivier et al., Science 1984 224:889). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported (Saunders and Williams, supra; D. E. Grigoriadis et al., *The CRF Receptor: Structure, Function and Potential for Therapeutic Intervention, Curr. Med. Chem.—Central Nervous System Agents* 2001 1:63-97; D. A. Gutman et al *Corticotropin-releasing factor antagonists as novel psychotherapeutics, Drugs of the Future* 2000 25(9):923-31).

CRF antagonists are effective in the treatment of a wide range of stress-related illnesses, mood disorders such as depression, major depressive disorder, single episode depression, recurrent depression, child abuse induced depression, postpartum depression, dysthemia, bipolar disorder and cyclothymia; chronic fatigue syndrome; eating disorders such as obesity, anorexia and bulimia nervosa; generalized anxiety disorder; panic disorder; phobias; obsessive-compulsive disorder; post-traumatic stress disorder; pain perception such as fibromyalgia; headache; stress-induced gastrointestinal dysfunction such as irritable bowel syndrome (IBS), colonic hypersensitivity or spastic colon; hemorrhagic stress; ulcers; stress-induced psychotic episodes; inflammatory disorders such as rheumatoid arthritis and osteoarthritis; asthma; psoriasis; allergies; premature birth; hypertension; congestive heart failure; sleep disorders; neurodegenerative diseases such as Alzheimer's disease, senile dementia, Parkinson's disease and Huntington's disease; head or spinal cord trauma; ischemic neuronal damage; excitotoxic neuronal damage; epilepsy; stroke; psychosocial dwarfism; chemical dependencies and addictions; drug and alcohol withdrawal symptoms; stress-induced immune dysfunctions; immune suppression and stress-induced infections; cardiovascular or heart related diseases; fertility problems; and/or human immunodeficiency virus infections. Accordingly clinical data suggests that CRF receptor antagonists may represent novel antidepressants and/or anxiolytic drugs that may be useful in the treatment of the neuropsychiatric disorders manifesting hypersecretion of CRF.

While significant strides have been made toward achieving CRF regulation by administration of CRF receptor antagonists, there remains a need in the art for efficacious and selective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

5,8-Dihydro-6H-pyrido[2,3-d]pyrimidin-7-ones have been reported with a variety of pharmacological activities. WO 200259083 (J. L. Adams et al.) discloses 5,8-dihydro-6H-pyrido[2,3-d]pyrimidin-7-one compounds which are p38 kinase. WO2001055148 (R. J. Booth et al.) and WO 98 33798 (D. H. Boschelli et al.) report related compounds with cyclin-dependent kinase inhibitory activity. WO 98 01428 (C. Dominguez et al.) disclose amidinoindoles, amidinoazoles and analogs as inhibitors of Factor Xa and of thrombin.

SUMMARY OF THE INVENTION

The present invention relates to CRF receptor antagonists, and more specifically to CRF receptor antagonist compounds according to formula I,

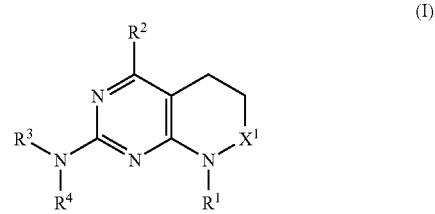

wherein,
X$^1$ is (CH$_2$)$_n$, or C=O;
n is 0 to 2;
R$^1$ is
(i) C$_{1-10}$ alkyl optionally substituted with a substituent selected from the group consisting of amino, C$_{1-3}$ alkylamino, C$_{1-3}$ dialkylamino, (C$_{1-3}$ alkyl)arylamino and phenyl, said phenyl optionally substituted with (a) one to three substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl,
(ii) $C_{3-7}$ cycloalkyl optionally substituted with $C_{1-3}$ alkyl,
(iii) $C_{3-7}$ cycloalkyl-$C_{1-3}$ alkyl,
(iv) benzofused-$C_{5-7}$ cycloalkyl,
(v) phenyl or heteroaryl said phenyl and heteroaryl optionally substituted with one to three substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl;
(vi) heteroaryl-$C_{1-6}$alkyl said heteroaryl-$C_{1-6}$alkyl optionally substituted with one to three substituents selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl;
(vii) 1,2-diphenylethyl,
(viii) $C_{1-3}$ alkoxy-$C_{1-6}$ alkyl, or,
(ix) aryloxy-$C_{1-6}$ alkyl said aryloxy group being optionally substituted with one to three substituents selected form the group consisting of $C_{1-3}$ alkyl, $C_{1-3}$ alkoxy and halogen;
$R^2$ is $C_{1-6}$ alkyl or $C_{1-3}$ haloalkyl;
$R^3$ is
(i) hydrogen,
(ii) $C_{1-6}$ alkyl optionally substituted with hydroxy, $C_{1-3}$ alkoxy or $C_{1-3}$ acyloxy,
(iii) $C_{3-6}$ alkenyl,
(iv) $C_{3-7}$ cycloalkyl,
(v) $C_{3-7}$ cycloalkyl-$C_{1-3}$ alkyl;
(vi) $C_{3-7}$ cycloalkenyl,
(vii) $C_{3-7}$ cycloalkenyl-$C_{1-3}$ alkyl,
(viii) benzyl optionally substituted with one to three groups independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl; and,
$R^4$ is aryl optionally substituted with one to three groups independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl; and
individual isomers, racemic or non-racemic mixtures of isomers, solvates, hydrates or pharmaceutically acceptable salts thereof The invention also relates to methods to treat a variety of disorders or illnesses, including stress-related disorders comprising administering an effective amount of a CRF receptor antagonist of this invention, preferably in the form of a pharmaceutical composition, to an animal in need thereof. The present invention also relates to pharmaceutical compositions containing one or more CRF receptor antagonists of this invention in combination with a pharmaceutically acceptable carrier and/or diluent. These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

In an embodiment of the present invention there is provided a compound according to formula I

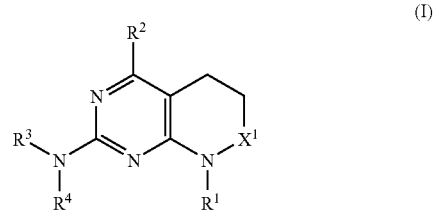

(I)

wherein $X^1$ is $(CH_2)_n$ and $R^1$, $R^2$, $R^3$, $R^4$ and n are as defined hereinabove.

In another embodiment of the present invention there is provided a compound according to formula I wherein $X^1$ is $(CH_2)_n$; n is 0; $R^1$ is (i) $C_{1-10}$ branched or unbranched alkyl, (ii) optionally substituted heteroaryl-$C_{1-6}$alkyl, said heteroaryl optionally substituted with a substituent selected from the group consisting of $C_{1-3}$ alkyl, $C_{1-3}$ alkoxy and halogen, (iii) optionally substituted phenyl or heteroaryl said phenyl or heteroaryl optionally substituted with a substituent selected from the group consisting of $C_{1-3}$ alkyl, $C_{1-3}$ alkoxy and halogen, or (iv) $C_{1-3}$ alkyl substituted with a phenyl said phenyl optionally substituted with a substituent selected from the group consisting of $C_{1-3}$ alkyl, $C_{1-3}$ alkoxy and halogen; $R^2$ is $C_{1-6}$ alkyl; $R^3$ is (i) hydrogen, (ii) $C_{1-6}$ alkyl, (iii) $C_{3-7}$ cycloalkyl-$C_{1-3}$ alkyl, or, (iv) benzyl optionally substituted with $C_{1-3}$ alkyl, $C_{1-3}$ alkoxy or halogen; $R^4$ is optionally substituted phenyl.

In another embodiment of the present invention there is provided a compound according to formula I wherein $X^1$ is $(CH_2)_n$; n is 0; $R^1$ is (i) $C_{1-10}$ branched or unbranched alkyl, (ii) $C_{1-10}$ alkyl substituted with a phenyl said phenyl optionally substituted, or (iii) heteroaryl-$C_{1-6}$ alkyl wherein said heteroaryl is 2-thienyl, 2-furanyl or 3-indolinyl each of said heteroaryl being optionally substituted; $R^2$ is $C_{1-6}$ alkyl; $R^3$ is (i) hydrogen, (ii) $C_{1-6}$ alkyl, (iii) $C_{3-7}$ cycloalkyl-$C_{1-3}$ alkyl, or, (iv) benzyl optionally substituted with $C_{1-3}$ alkyl, $C_{1-3}$ alkoxy or halogen; $R^4$ is optionally substituted phenyl.

In another embodiment of the present invention there is provided a compound according to formula I wherein $X^1$ is $(CH_2)_n$; n is 0; $R^1$ is (i) $C_{1-10}$ branched or unbranched alkyl, (ii) $C_{1-10}$ alkyl substituted with a phenyl said phenyl optionally substituted, or (iii) heteroaryl-$C_{1-6}$ alkyl wherein said heteroaryl is 2-thienyl, 2-furanyl or 3-indolinyl each of said heteroaryl being optionally substituted; $R^2$ is $C_{1-6}$ alkyl; $R^3$ is (i) hydrogen, (ii) $C_{1-6}$ alkyl, (iii) $C_{3-7}$ cycloalkyl-$C_{1-3}$ alkyl, or, (iv) benzyl optionally substituted with $C_{1-3}$ alkyl, $C_{1-3}$ alkoxy or halogen; $R^4$ is 2,4-disubstituted- or 2,4,6-trisubstituted-phenyl.

In another embodiment of the present invention there is provided a compound according to formula I wherein $X^1$ is $(CH_2)_n$; n is 1; $R^1$ is (i) $C_{1-10}$ branched or unbranched alkyl, (ii) optionally substituted heteroaryl-$C_{1-6}$alkyl, said heteroaryl optionally substituted with a substituent selected from the group consisting of $C_{1-3}$ alkyl, $C_{1-3}$ alkoxy and halogen, (iii) optionally substituted phenyl or heteroaryl said phenyl or heteroaryl optionally substituted with a substituent selected from the group consisting of $C_{1-3}$ alkyl, $C_{1-3}$ alkoxy and halogen, or (iv) $C_{1-3}$ alkyl substituted with a phenyl said phenyl optionally substituted with a substituent selected from the group consisting of $C_{1-3}$ alkyl, $C_{1-3}$ alkoxy and halogen; $R^2$ is $C_{1-6}$ alkyl or $C_{1-3}$ haloalkyl; $R^3$ is (i) hydrogen, (ii) $C_{1-6}$ alkyl, (iii) $C_{3-7}$ cycloalkyl-$C_{1-3}$ alkyl, or, (iv) benzyl optionally substituted with $C_{1-3}$ alkyl, $C_{1-3}$ alkoxy or halogen; $R^4$ is optionally substituted phenyl.

In another embodiment of the present invention there is provided a compound according to formula I wherein $X^1$ is $(CH_2)_n$; n is 1; $R^1$ is (i) $C_{1-10}$ branched or unbranched alkyl, (ii) optionally substituted heteroaryl-$C_{1-6}$alkyl, said heteroaryl optionally substituted with a substituent selected from the group consisting of $C_{1-3}$ alkyl, $C_{1-3}$ alkoxy and halogen, (iii) optionally substituted phenyl or heteroaryl said phenyl or heteroaryl optionally substituted with a substituent selected from the group consisting of $C_{1-3}$ alkyl, $C_{1-3}$ alkoxy and halogen, or (iv) $C_{1-3}$ alkyl substituted with a phenyl said phenyl optionally substituted with a substituent selected from the group consisting of $C_{1-3}$ alkyl, $C_{1-3}$ alkoxy and halogen; $R^2$ is $C_{1-6}$ alkyl or $C_{1-3}$ haloalkyl; $R^3$ is (i) hydrogen, (ii) $C_{1-6}$ alkyl, (iii) $C_{3-7}$ cycloalkyl-$C_{1-3}$ alkyl, or, (iv) benzyl optionally substituted with $C_{1-3}$ alkyl, $C_{1-3}$ alkoxy or halogen; $R^4$ is 2,4-disubstituted- or 2,4,6-trisubstituted-phenyl.

In another embodiment of the present invention there is provided a compound according to formula I wherein $X^1$ is $(CH_2)_n$; n is 2; $R^1$ is (i) $C_{1-10}$ branched or unbranched alkyl, (ii) optionally substituted heteroaryl-$C_{1-6}$alkyl, said heteroaryl optionally substituted with a substituent selected from the group consisting of $C_{1-3}$ alkyl, $C_{1-3}$ alkoxy and halogen, (iii) optionally substituted phenyl or heteroaryl said phenyl or heteroaryl optionally substituted with a substituent selected from the group consisting of $C_{1-3}$ alkyl, $C_{1-3}$ alkoxy and halogen, or (iv) $C_{1-3}$ alkyl substituted with a phenyl said phenyl optionally substituted with a substituent selected from the group consisting of $C_{1-3}$ alkyl, $C_{1-3}$ alkoxy and halogen; $R^2$ is $C_{1-6}$ alkyl or $C_{1-3}$ haloalkyl; $R^3$ is (i) hydrogen, (ii) $C_{1-6}$ alkyl, (iii) $C_{3-7}$ cycloalkyl-$C_{1-3}$ alkyl, or, (iv) benzyl optionally substituted with $C_{1-3}$ alkyl, $C_{1-3}$ alkoxy or halogen; $R^4$ is optionally substituted phenyl.

In another embodiment of the present invention there is provided a compound according to formula I wherein $X^1$ is $(CH_2)_n$; n is 2; $R^1$ is (i) $C_{1-10}$ branched or unbranched alkyl, (ii) optionally substituted heteroaryl-$C_{1-6}$alkyl, said heteroaryl optionally substituted with a substituent selected from the group consisting of $C_{1-3}$ alkyl, $C_{1-3}$ alkoxy and halogen, (iii) optionally substituted phenyl or heteroaryl said phenyl or heteroaryl optionally substituted with a substituent selected from the group consisting of $C_{1-3}$ alkyl, $C_{1-3}$ alkoxy and halogen, or (iv) $C_{1-3}$ alkyl substituted with a phenyl said phenyl optionally substituted with a substituent selected from the group consisting of $C_{1-3}$ alkyl, $C_{1-3}$ alkoxy and halogen; $R^2$ is $C_{1-6}$ alkyl or $C_{1-3}$ haloalkyl; $R^3$ is (i) hydrogen, (ii) $C_{1-6}$ alkyl, (iii) $C_{3-7}$ cycloalkyl-$C_{1-3}$ alkyl, or, (iv) benzyl optionally substituted with $C_{1-3}$ alkyl, $C_{1-3}$ alkoxy or halogen; $R^4$ is 2,4-disubstituted- or 2,4,6-trisubstituted-phenyl.

In another embodiment of the present invention there is provided a method for treating a subject having a disease state that is alleviated by treatment with a CRF receptor antagonist, which comprises administering to a patient in need thereof a therapeutically effective amount of a compound of formula I wherein $X^1$, $R^1$, $R^2$, $R^3$, $R^4$ and n are as defined hereinabove.

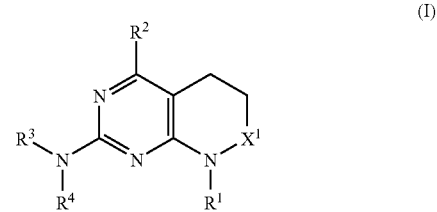

(I)

In another embodiment of the present invention there is provided a method of treating phobias, stress-related illnesses, mood disorders, eating disorders, generalized anxiety disorders, stress-induced gastrointestinal dysfunctions, neurodegenerative diseases, and neuropsychiatric disorders which comprises administering to a patient in need thereof a therapeutically effective amount of a compound of formula I: wherein $X^1$, $R^1$, $R^2$, $R^3$, $R^4$ and n are as defined hereinabove.

In another embodiment of the present invention there is provided a pharmaceutical composition for treating a subject having a disease state that is alleviated by treatment with a CRF receptor antagonist comprising a therapeutically effective amount of at least one compound of formula I

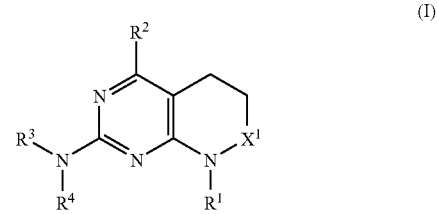

(I)

wherein $X^1$, $R^1$, $R^2$, $R^3$, $R^4$ and n are as defined hereinabove in admixture with at least one pharmaceutically acceptable carrier, diluent or excipient.

In another embodiment of the present invention there is provided a process for preparing a compound according to formula I wherein $R^3$ is hydrogen and $X^1$, $R^1$, $R^2$, $R^4$ and n are as defined hereinabove comprising the steps of:

(i) contacting an aryl amine hydrochloride XXII wherein $R^4$ is as defined above with cyanamid to afford an aryl guanidinium hydrochloride XXIII;

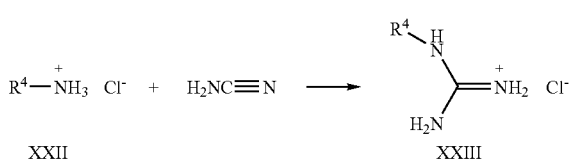

(ii) contacting said guanidine hydrochloride XXIII with a α-substituted β-keto ester XXIV wherein $R^2$ is $C_{1-6}$ alkyl and $R^6$ is $C_{1-6}$ alkyl and $R^7$ is alkoxycarbonylalkyl or $R^6$ and $R^7$ together are $(CH_2)_o$ and o is 2 to 4 in the presence of base to afford the pyrimidine XXV wherein $R^5$ is alkoxycarbonylalkyl or $(CH_2)_o$—OH;

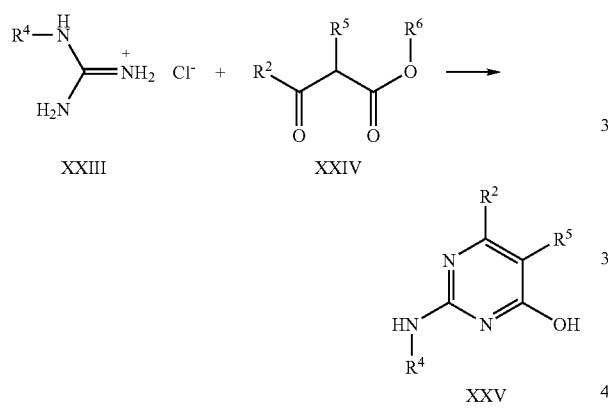

(iii) contacting said pyrimidine with a chlorinating agent sufficiently reactive to convert XXV to the corresponding chloropyrimidine XXVI and to convert a hydroxyalkylene side chain present at $R^5$ to the corresponding chloroalkylene substituent;

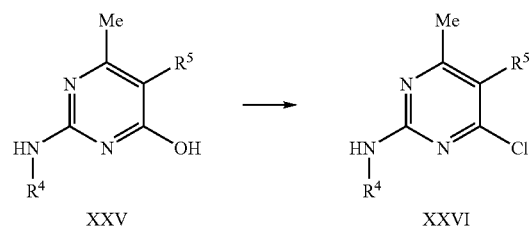

(iv) contacting said chloropyrimidine XXVI with a primary amine under conditions which displace the chlorine atoms on the pyrimidine and the $R^5$ side chain when $R^5$ is hydroxyalkylene resulting in the formation of the fused heterocyclic ring XXVII wherein $R^5$ is $(CH_2)_o$ or which displace the chlorine on the pyrimidine and concomitantly cyclize to a lactam when $R^5$ is an alkoxycarbonyl alkyl.

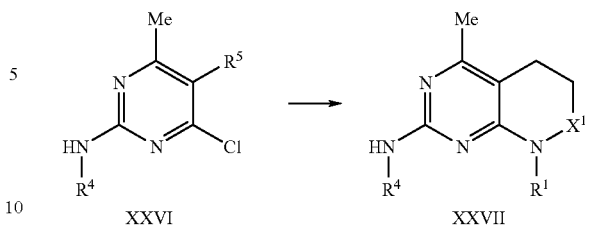

In another embodiment of the present invention there is provided a process for the preparation of a compound according to formula I wherein $X^1$, $R^1$, $R^2$, $R^4$ and n are as defined hereinabove and $R^3$ is (i) $C_{1-6}$ alkyl optionally substituted with hydroxy, $C_{1-3}$ alkoxy or $C_{1-3}$ acyloxy, (ii) $C_{3-6}$ alkenyl, (iii) $C_{3-7}$ cycloalkyl, (iv) $C_{3-7}$ cycloalkyl-$C_{1-3}$ alkyl; (v) $C_{3-7}$ cycloalkenyl, (vi) $C_{3-7}$ cycloalkenyl-$C_{1-3}$ benzyl optionally substituted with one to three groups independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl; wherein steps (i) to (iv) are carried out as described above and the pyrimidine XXVII wherein $R^3$ is hydrogen is further contacted with base and an alkylating agent to afford the tertiary amine according to formula XXVIII.

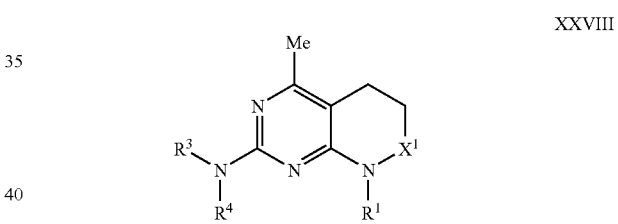

In another embodiment of the present invention there is provided a process for the preparation of a compound according to formula I wherein $X^1$ is $(CH_2)_n$, $R^1$, $R^2$, $R^3$, $R^4$ and n are as defined hereinabove wherein a lactam according to formula XXVIII wherein $X^1$ is C=O is contacted with a reducing agent to afford the amine according to formula I wherein $X^1$ is $CH_2$.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the moiety may be hydrogen or a substituent.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl wherein alkyl is composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "alkylene" as used herein denotes a divalent linear or branched saturated hydrocarbon radical, having from one to six carbons inclusive, unless otherwise indicated. Examples of alkylene radicals include, but are not limited to, methylene, ethylene, propylene, 2-methyl-propylene, butylene, and 2-ethylbutylene.

The term "alkenyl" as used herein denotes an unsubstituted hydrocarbon chain radical having from 2 to 10 carbon atoms having one or two olefinic double bonds [preferably one olefinic double bond]. $C_{2-10}$ alkenyl" as used herein refers to an alkenyl composed of 2 to 10 carbons. Examples are vinyl, 1-propenyl, 2-propenyl (allyl) or 2-butenyl (crotyl).

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. The term "$C_{3-7}$ cycloalkyl" as used herein refers to an cycloalkyl composed of 3 to 7 carbons in the carbocyclic ring.

The term "benzofused-$C_{5-7}$ cycloalkyl" as used herein refers a saturated carbocyclic ring containing 5 to 7 carbon atoms wherein two adjacent carbons of the cycloalkyl group are linked by a double bond and said two adjacent carbons are substituted by —(CH═CH)$_2$— and the benzofused cycloalkyl is linked at the cycloalkyl group.

The term "cycloalkylalkyl" as used herein refers to the radical R'R"—, wherein R' is a cycloalkyl radical as defined herein, and R" is an alkyl radical as defined herein. Examples of cycloalkylalkyl radicals include, but are not limited to, cyclopropylmethyl, cyclohexylmethyl, cyclopentylethyl and the attachment point of the cycloalkylalkyl radical will be on the alkylene radical. $C_{3-7}$ cycloalkyl-$C_{1-3}$ alkyl refers to the radical R'R" where R' is $C_{3-7}$ cyclolalkyl and R" is $C_{1-3}$ alkylene as defined herein.

The term "acyl" as used herein denotes a group of formula C(═O)R wherein R is hydrogen or lower alkyl as defined herein. The term or "alkylcarbonyl" as used herein denotes a group of formula C(═O)R wherein R is alkyl as defined herein. The term "arylcarbonyl" as used herein means a group of formula C(═O)R wherein R is an aryl group; the term "benzoyl" as used herein an "arylcarbonyl" group wherein R is phenyl.

The term "acyloxy" as used herein denotes the radical —OC(O)R, wherein R is a lower alkyl radical as defined herein. Examples of acyloxy radicals include, but are not limited to, acetoxy, propionyloxy.

The terms "amino", "alkylamino" and "dialkylamino" as used herein refer to —NH$_2$, —NHR and —NR$_2$ respectively and R is alkyl as defined above. The two alkyl groups attached to a nitrogen in a dialkyl moiety can be the same or different.

The term "(alkyl)arylamino" as used herein refers to the radical R'R" where R' is —NH(aryl) and R" is alkylene as defined herein with the understanding that the attachment point of the (alkyl)arylamino moiety will be on the alkylene radical.

The term "alkoxy group" means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl including their isomers.

The terms "alkoxycarbonylalkyl" and "aryloxycarbonylalkyl" as used herein denotes the radical R'R" where R' is an alkoxycarbonyl or aryloxycarbonyl radical and R" is alkylene as defined herein and the attachment point of the aryl(alkoxy)carbonylalkyl radical will be on the alkylene radical.

The term "alkylthio" or "thioalkyl group" means an —S-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkylthio" or "lower thioalkyl" as used herein denotes an alkylthio group with a "lower alkyl" group as previously defined. "$C_{1-10}$ alkylthio" as used herein refers to an-S-alkyl wherein alkyl is $C_{1-10}$.

The terms "alkylsulfonyl" and "arylsulfonyl" as used herein denotes a group of formula —S(═O)$_2$R wherein R is alkyl or aryl respectively and alkyl and aryl are as defined herein.

The term "aminosulfonyl" as used herein refers to the radical —S(O)$_2$NH$_2$. The terms "alkylaminosulfonyl" and "dialkylaminosulfonyl" as used herein refer to the radical —S(O)$_2$NR'R", wherein R' and R" are hydrogen and lower alkyl or R' and R" are independently lower alkyl respectively. Examples of alkylaminosulfonyl include, but are not limited to methylaminosulfonyl, iso-propylaminosulfonyl. Examples of dialkylaminosulfonyl include, but are not limited to dimethylaminosulfonyl, iso-propyl-methylaminosulfonyl.

The term "aryl" as used herein denotes a monovalent aromatic carbocyclic radical consisting of one individual ring, or one or more fused rings in which at least one ring is aromatic in nature, which can optionally be substituted with one or more, preferably one or two, substituents selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group. Examples of aryl radicals include, but are not limited to, phenyl, naphthyl, biphenyl, indanyl, anthraquinolyl.

The term "aryloxy" as used herein denotes a O-aryl group, wherein aryl is as defined above. An aryloxy group can be unsubstituted or substituted with one or two suitable substituents. The term "phenoxy" refers to an aryloxy group wherein the aryl moiety is a phenyl ring.

The term "aryloxyalkyl" as used herein denotes the radical R'R"—, wherein R' is an aryloxy radical as defined herein, and R" is an alkylene radical as defined herein with the understanding that the attachment point of the aryloxyalkyl moiety will be on the alkylene radical. Aryloxy-$C_{1-3}$ alkyl refers to the radical R'R" where R' is an aryloxy radical and R" is $C_{1-3}$ alkylene as defined herein.

The term "cycloalkenyl" as used herein denotes a unsaturated carbocyclic ring containing 4 to 8 carbon atoms, i.e. cyclobutenyl, cyclopentenyl, cyclohexenyl, cycloheptyl or cyclooctenyl. "$C_{4-7}$ cycloalkenyl" as used herein refers to an cycloalkenyl composed of 4 to 7 carbons in the carbocyclic ring.

The term "cycloalkenylalkyl" as used herein refers to the radical R'R"—, wherein R' is a cycloalkenyl radical as defined herein, and R" is an alkylene radical as defined herein with the understanding that the attachment point of the cycloalkenylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cyclolalkyl and R" is $C_{1-3}$ alkylene as defined herein.

The term "halogen" or "halo" as used herein means fluorine, chlorine, bromine, or iodine.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazolyl, isoxazolyl, thiazolyl, isothiazolyl, triazolinyl, thiadiazolinyl and oxadiazolinyl which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl and dialkylcarbamoyl. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring.

The term "heteroarylalkyl" or "heteroaralkyl" means the radical of the formula R'R", wherein R' is an optionally substituted heteroaryl radical as defined herein, and R" is an alkylene radical as defined herein with the understanding that the attachment point of the heteroaryl radical will be on the alkylene radical. Examples of heteroarylalky radicals include, but are not limited to, 2-imidazolylmethyl, 3-pyrrolylethyl.

The terms "hydroxyalkylene" as used herein denotes the radical R'R" where R' is an hydroxy radical and R" is alkylene as defined herein and the attachment point of the hydroxyalkylene radical will be on the alkylene radical.

The terms "chloroalkylene" as used herein denotes the radical R'R" where R' is an chlorine radical and R" is alkylene as defined herein and the attachment point of the chloroalkylene radical will be on the alkylene radical.

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 140. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it

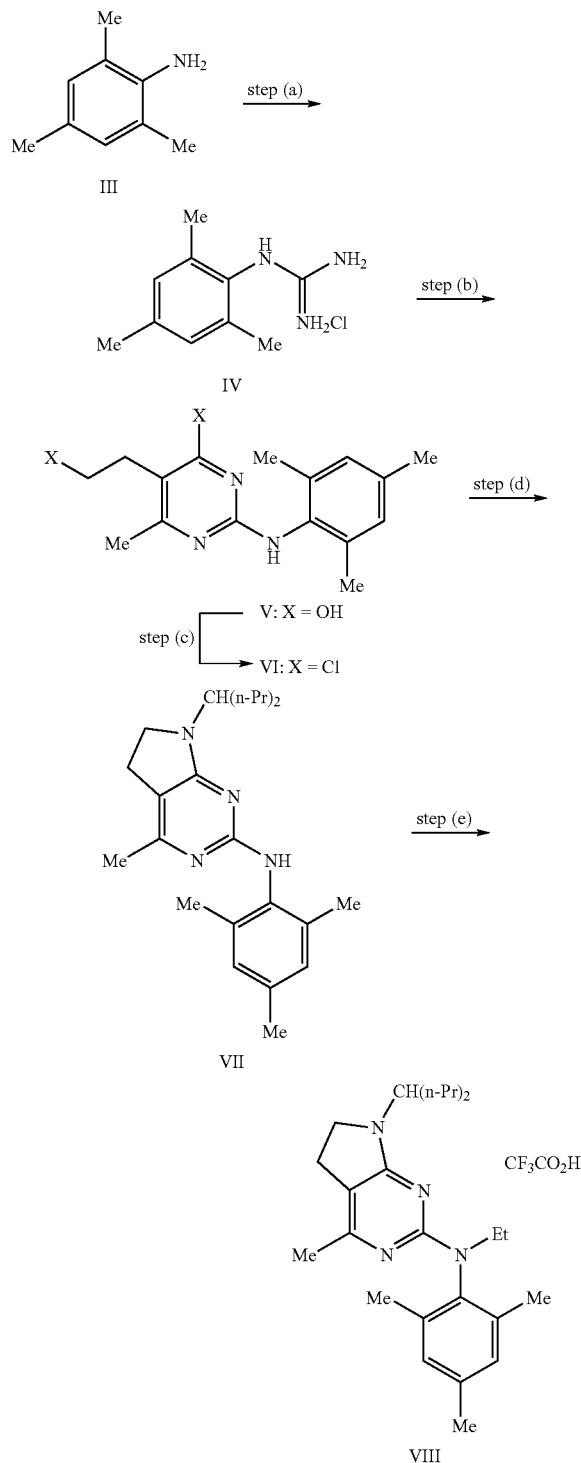

(a) HCl (1.0 equiv), cyanamid (1.2 equiv), EtOH, reflux, 43 h (100%); (b) NaOMe (1.0 equiv), 2-acetylbutyrolactone (1.0 equiv), EtOH—MeOH, reflux, 19 h (38%); (c) SOCl$_2$ (1.05 equiv), toluene, room temperature, 69 h, then POCl$_3$ (24 equiv, neat), reflux, 15 h (92%); (d) 4-aminoheptane (5.0 equiv), NMP, 120° C., 50 h (41%); (e) NaH (1.5 equiv), iodoethane (1.5 equiv), DMF, room temperature, 8 h, then 40° C., 12 h (purified by preparatory RP-HPLC as TFA salt).

[4-Methyl-7-(1-propyl-butyl)-6,7-dihydro-5H-pyrrolo[2,3-d]pyrimidin-2-yl]-(2,4,6-trimethyl-phenyl)-amine (VII) is prepared by sequentially elaborating a substituted pyrimidine ring containing the elements required for subsequent formation of the fused dihydropyrrole ring. The Principal Synthesis provides and extremely general approach to preparing the pyrimidine ring. The Principal synthesis entails condensation of two three-atom fragments. One fragment is a β-dicarbonyl compound. The carbonyls may be composed of ketones, aldehydes, carboxylic acid derivatives or nitriles. The second three atom segment is amidine which can be replaced by a urea, thiourea or guanidine. The range of equivalents capable of undergoing this reaction affords significant flexibility in the preparation of substituted pyrimidines. (D. J. Brown *Pyrimidines and their benzo Derivatives in Comprehensive Heterocyclic Chemistry*, A. J. Boulton and A. McKillop (ed) vol. 3 part 2b, chap. 2.13, Pergamon Press, Oxford 1984 pp. 57-15[7]; D. J. Brown, *The Pyrimidines, Supplement II* in *The Chemistry of Heterocyclic Compounds*, A. Weissberger and E. C. Taylor (ed), Wiley Interscience, New York 1985, pp. 21-62)

In the present case the 2 arylamino-substituted pyrimidines can be directly prepared by utilization of an aryl guanidine in the cyclization step. Aryl guanidines are readily prepared from aryl amines (I. A. Cliffe *Functional Groups Containing an Iminocarbonyl Group and Any Element Other than A Halogen or Chalogen* in *Comprehensive Functional Group Transformations*, Vol 6, T. L. Gilchrist (ed) Pergamon Press, Oxford, 1995, pp. 640-42) In step (i) an appropriately substituted aryl amine is converted to the corresponding guanidinium hydrochloride salt by condensation with cyanamid.

Step (b) exemplifies the Principal pyrimidine synthesis wherein a 2-arylaminopyrimidine is prepared by cyclization of the guanidine and 2-acetylbutyrolactone which introduces the desired 2-arylamino and 4-methyl substituents onto the pyrimidine ring in addition to the hydroxy ethyl moiety and the 6-hydroxy group which ultimately is cyclized to produce the fused pyrrolidine. One skilled in the art will readily appreciate that 2-acetylbutyrolactone formally is simply a 2-substituted acetoacetic acid derivative and the pyrimidine synthesis can be accomplished with variety of side chains which can alter the sized and substitution on the heterocyclic ring fused to the pyrimidine.

Hydroxy pyrimidines can be converted to halopyrimidines by treating the pyrimidinone with a phosphoryl halide, a phosphorus pentahalide, a phosphorus trihalide or mixtures thereof. Tertiary amine bases are sometimes used as catalysts for the halogenation. The halogenation reaction can be run in the presence of a variety of functional groups without interference (Brown *Comprehensive Heterocyclic Chemistry*, supra p 139-140). In step (b) two chlorinations are carried out by sequential treatment of the diol VI with (a) thionyl chloride at room temperature which converts the hydroxyethyl side chain to the corresponding chloroethyl side chain and (b) phosphorus oxychloride at reflux which results in the conversion of the heteroaryl hydroxy substituent to the heteroaryl chloro moiety.

Amine substituents are readily introduced into a pyrimidine by displacement of leaving groups on the pyrimidine (Brown *Comprehensive Heterocyclic Chemistry*, supra p. 129-133). Among the leaving groups which can be employed are halogen, mercapto, alkylthio, alkylsulfonyl, alkylsulfinyl and alkoxy. Halogen and alkylsulfonyl are the most efficient leaving groups. Reactivity is generally 4 or 6 halo>2-halo>>5-halo. In step (d) the dichloro intermediate is treated with a primary amine which capable of displacing both the aliphatic chloride and the heteroaryl chloride thereby resulting in closure of the pyrrolidine ring.

Optionally in step (e) the secondary amine can be converted to a tertiary amine by formation of the amine salt and alkylation with the desired alkyl halide (J. March, *Advanced Organic Chemistry*, John Wiley & Sons, New York 1992, pp. 411-413). The product can either be a free base or an acid addition salt.

The following compounds were prepared as described in Scheme 1 by selection of the appropriate aryl amine in step (a) and the appropriate primary amine in step (e).

TABLE 1

| cpd # | Structure | Name | mp (° C.) | [M + H]+ calc'd. observed |
|---|---|---|---|---|
| 1 | 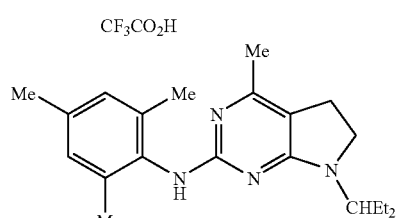 | [7-(1-Ethyl-propyl)-4-methyl-6,7-dihydro-5H-pyrrolo[2,3-d]pyrimidin-2-yl]-(2,4,6-trimethylphenyl)-amine; compound with trifluoro-acetic acid | | 339.5<br>339 |
| 2 | 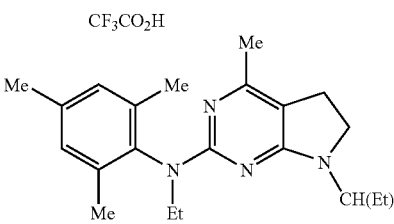 | Ethyl-[7-(1-ethyl-propyl)-4-methyl-6,7-dihydro-5H-pyrrolo[2,3-d]pyrimidin-2-yl]-(2,4,6-trimethyl-phenyl)-amine; compound with trifluoro-acetic acid | | 367.6<br>367 |
| 3 | 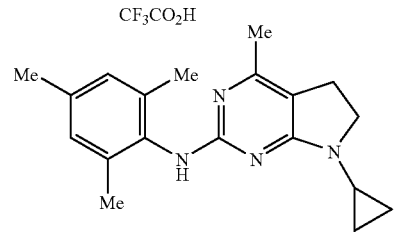 | (7-Cyclopropyl-4-methyl-6,7-dihydro-5H-pyrrolo[2,3-d]pyrimidin-2-yl)-(2,4,6-trimethyl-phenyl)-amine; compound with trifluoro-acetic acid | | 309.4<br>309 |
| 4 | 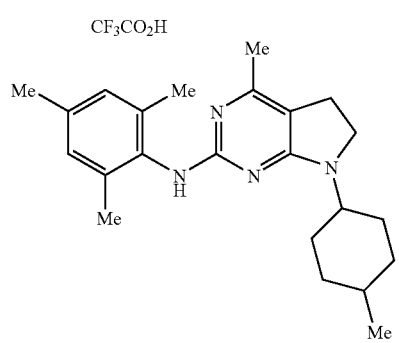 | [4-Methyl-7-(4-methyl-cyclohexyl)-6,7-dihydro-5H-pyrrolo[2,3-d]pyrimidin-2-yl]-(2,4,6-trimethyl-phenyl)-amine; compound with trifluoro-acetic acid | | 365.5<br>365 |

TABLE 1-continued

| cpd # | Structure | Name | mp (° C.) | [M + H]+ calc'd. observed |
|---|---|---|---|---|
| 5 | 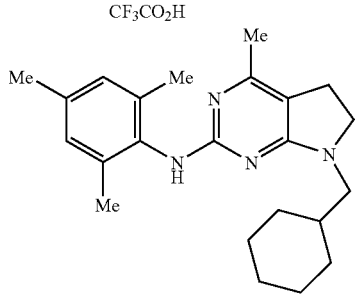 | (7-Cyclohexylmethyl-4-methyl-6,7-dihydro-5H-pyrrolo[2,3-d]pyrimidin-2-yl)-(2,4,6-trimethyl-phenyl)-amine; compound with trifluoro-acetic acid | | 365.5 365 |
| 6 | 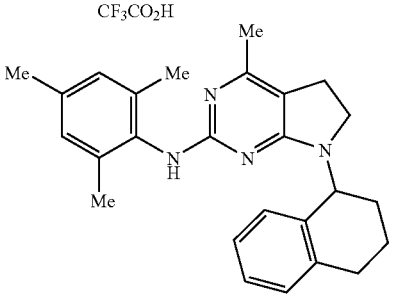 | [4-Methyl-7-(1,2,3,4-tetrahydro-naphthalen-1-yl)-6,7-dihydro-5H-pyrrolo[2,3-d]pyrimidin-2-yl]-(2,4,6-trimethyl-phenyl)-amine; compound with trifluoro-acetic acid | | 399.6 399 |
| 7 | 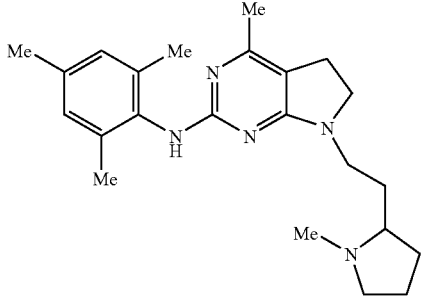 | {4-Methyl-7-[2-(1-methyl-pyrrolidin-2-yl)-ethyl]-6,7-dihydro-5H-pyrrolo[2,3-d]pyrimidin-2-yl}-(2,4,6-trimethyl-phenyl)-amine; compound with trifluoro-acetic acid | | 380.5 380 |
| 8 | 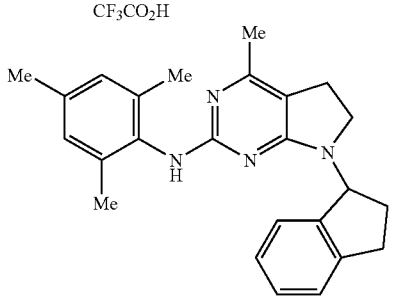 | (7-Indan-1-yl-4-methyl-6,7-dihydro-5H-pyrrolo[2,3-d]pyrimidin-2-yl)-(2,4,6-trimethyl-phenyl)-amine; compound with trifluoro-acetic acid | | 385.5 385 |

TABLE 1-continued

| cpd # | Structure | Name | mp (° C.) | [M + H]+ calc'd. observed |
|---|---|---|---|---|
| 9 | 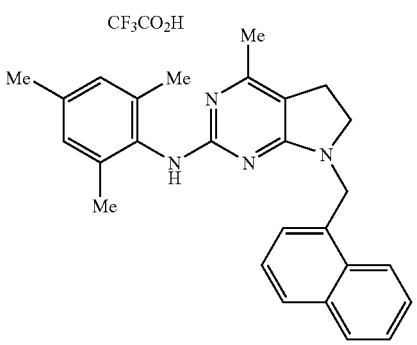 | (4-Methyl-7-naphthalen-1-yl-methyl-6,7-dihydro-5H-pyrrolo[2,3-d]pyrimidin-2-yl)-(2,4,6-trimethyl-phenyl)-amine; compound with trifluoro-acetic acid | | 409.5 409 |
| 10 | 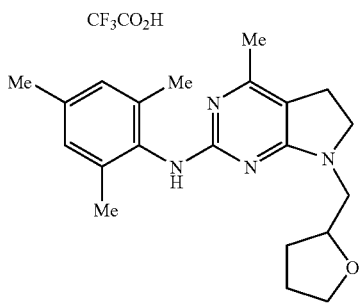 | [4-Methyl-7-(tetrahydro-furan-2-yl-methyl)-6,7-dihydro-5H-pyrrolo[2,3-d]pyrimidin-2-yl]-(2,4,6-trimethyl-phenyl)-amine; compound with trifluoro-acetic acid | | 353.5 353 |
| 11 | 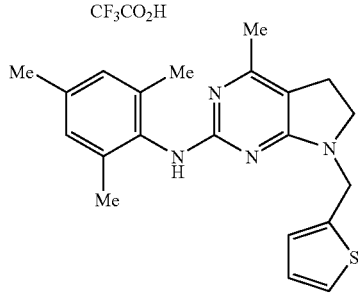 | (4-Methyl-7-thiophen-2-ylmethyl-6,7-dihydro-5H-pyrrolo[2,3-d]pyrimidin-2-yl)-(2,4,6-trimethyl-phenyl)-amine; compound with trifluoro-acetic acid | | 365.5 365 |
| 12 | 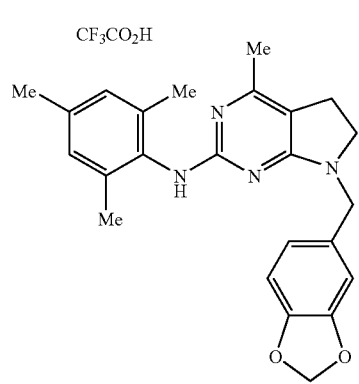 | (7-Benzo[1,3]dioxol-5-ylmethyl-4-methyl-6,7-dihydro-5H-pyrrolo[2,3-d]pyrimidin-2-yl)-(2,4,6-trimethyl-phenyl)-amine; compound with trifluoro-acetic acid | | 403.5 403 |

TABLE 1-continued

| cpd # | Structure | Name | mp (° C.) | [M + H]+ calc'd. observed |
|---|---|---|---|---|
| 13 | 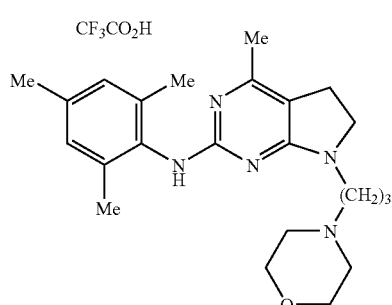 | [4-Methyl-7-(3-morpholin-4-yl-propyl)-6,7-dihydro-5H-pyrrolo[2,3-d]pyrimidin-2-yl]-(2,4,6-trimethyl-phenyl)-amine; compound with trifluoro-acetic acid | | 396.5 396 |
| 14 | 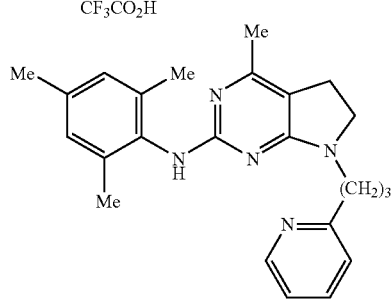 | [4-Methyl-7-(2-pyridin-2-yl-ethyl)-6,7-dihydro-5H-pyrrolo[2,3-d]pyrimidin-2-yl]-(2,4,6-trimethyl-phenyl)-amine; compound with trifluoro-acetic acid | | 374.5 374 |
| 15 | 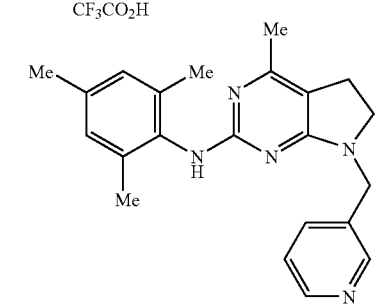 | (4-Methyl-7-pyridin-3-ylmethyl-6,7-dihydro-5H-pyrrolo[2,3-d]pyrimidin-2-yl)-(2,4,6-trimethyl-phenyl)-amine; compound with trifluoro-acetic acid | | 360.5 360 |
| 16 | 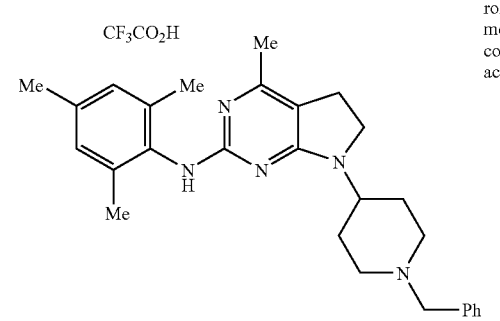 | [7-(1-Benzyl-piperidin-4-yl)-4-methyl-6,7-dihydro-5H-pyrrolo[2,3-d]pyrimidin-2-yl]-(2,4,6-trimethyl-phenyl)-amine; compound with trifluoro-acetic acid | | 442.6 442 |

TABLE 1-continued

| cpd # | Structure | Name | mp (° C.) | [M + H]+ calc'd. observed |
|---|---|---|---|---|
| 17 | CF$_3$CO$_2$H (structure) | [4-Methyl-7-(2-piperidin-1-yl-ethyl)-6,7-dihydro-5H-pyrrolo[2,3-d]pyrimidin-2-yl]-(2,4,6-trimethyl-phenyl)-amine; compound with trifluoro-acetic acid | | 380.5 380 |
| 18 | CF$_3$CO$_2$H (structure) | [7-(1,2-Diphenyl-ethyl)-4-methyl-6,7-dihydro-5H-pyrrolo[2,3-d]pyrimidin-2-yl]-(2,4,6-trimethyl-phenyl)-amine; compound with trifluoro-acetic acid | | 449.6 449 |
| 19 | CF$_3$CO$_2$H (structure) | (7-Isopropyl-4-methyl-6,7-dihydro-5H-pyrrolo[2,3-d]pyrimidin-2-yl)-(2,4,6-trimethyl-phenyl)-amine; compound with trifluoro-acetic acid | | 311.4 311 |
| 20 | CF$_3$CO$_2$H (structure) | [7-(2-Methoxy-1-methyl-ethyl)-4-methyl-6,7-dihydro-5H-pyrrolo[2,3-d]pyrimidin-2-yl]-(2,4,6-trimethyl-phenyl)-amine; compound with trifluoro-acetic acid | | 341.5 341 |
| 21 | CF$_3$CO$_2$H (structure) | [4-Methyl-7-(1-methyl-3-phenyl-propyl)-6,7-dihydro-5H-pyrrolo[2,3-d]pyrimidin-2-yl]-(2,4,6-trimethyl-phenyl)-amine; compound with trifluoro-acetic acid | | 401.6 401 |
| 22 | CF$_3$CO$_2$H (structure) | (7-Benzyl-4-methyl-6,7-dihydro-5H-pyrrolo[2,3-d]pyrimidin-2-yl)-(2,4,6-trimethyl-phenyl)-amine; compound with trifluoro-acetic acid | | 359.5 359 |

TABLE 1-continued

| cpd # | Structure | Name | mp (° C.) | [M + H]+ calc'd. observed |
|---|---|---|---|---|
| 23 | 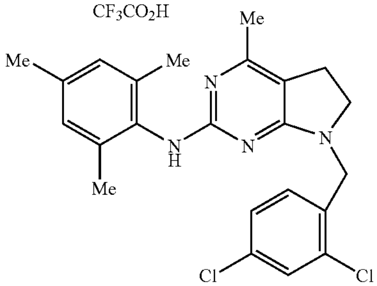 | [7-(2,4-Dichloro-benzyl)-4-methyl-6,7-dihydro-5H-pyrrolo[2,3-d]pyrimidin-2-yl]-(2,4,6-trimethyl-phenyl)-amine; compound with trifluoro-acetic acid | | 427.4<br>427 |
| 24 | 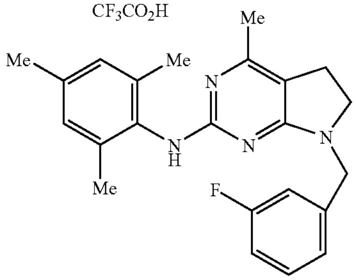 | [7-(3-Fluoro-benzyl)-4-methyl-6,7-dihydro-5H-pyrrolo[2,3-d]pyrimidin-2-yl]-(2,4,6-trimethyl-phenyl)-amine; compound with trifluoro-acetic acid | | 377.5<br>377 |
| 25 | 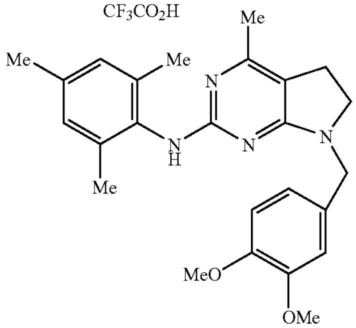 | [7-(3,4-Dimethoxy-benzyl)-4-methyl-6,7-dihydro-5H-pyrrolo[2,3-d]pyrimidin-2-yl]-(2,4,6-trimethyl-phenyl)-amine; compound with trifluoro-acetic acid | | 419.5<br>419 |
| 26 | 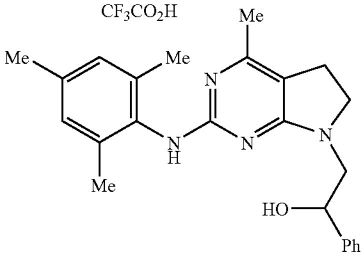 | 2-[4-Methyl-2-(2,4,6-trimethyl-phenyl-amino)-5,6-dihydro-pyrrolo[2,3-d]pyrimidin-7-yl]-1-phenyl-ethanol; compound with trifluoro-acetic acid | | 389.5<br>389 |
| 27 | 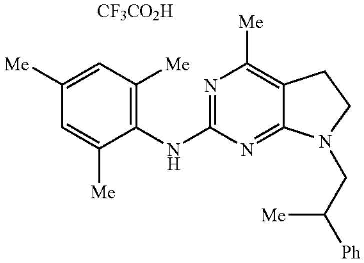 | [4-Methyl-7-(2-phenyl-propyl)-6,7-dihydro-5H-pyrrolo[2,3-d]pyrimidin-2-yl]-(2,4,6-trimethyl-phenyl)-amine; compound with trifluoro-acetic acid | | 387.5<br>387 |

TABLE 1-continued

| cpd # | Structure | Name | mp (° C.) | [M + H]+ calc'd. observed |
|---|---|---|---|---|
| 28 | 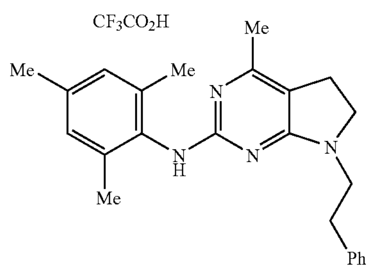 | (4-Methyl-7-phenethyl-6,7-dihydro-5H-pyrrolo[2,3-d]pyrimidin-2-yl)-(2,4,6-trimethyl-phenyl)-amine; compound with trifluoro-acetic acid | | 373.5<br>373 |
| 29 | 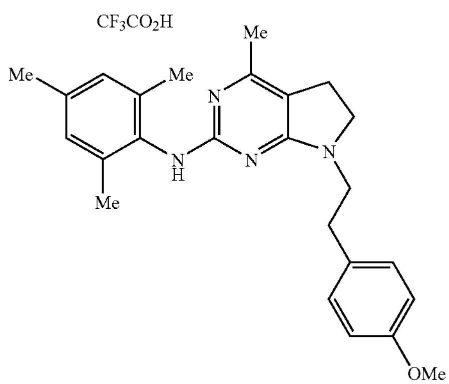 | {7-[2-(4-Methoxy-phenyl)-ethyl]-4-methyl-6,7-dihydro-5H-pyrrolo[2,3-d]pyrimidin-2-yl}-(2,4,6-trimethyl-phenyl)-amine; compound with trifluoro-acetic acid | | 403.5<br>403 |
| 30 | 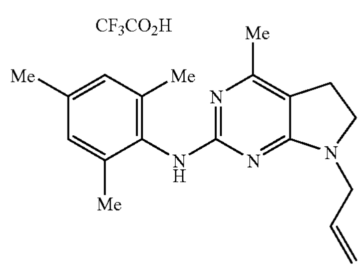 | (7-Allyl-4-methyl-6,7-dihydro-5H-pyrrolo[2,3-d]pyrimidin-2-yl)-(2,4,6-trimethyl-phenyl)-amine; compound with trifluoro-acetic acid | | 309.4<br>309 |
| 31 | 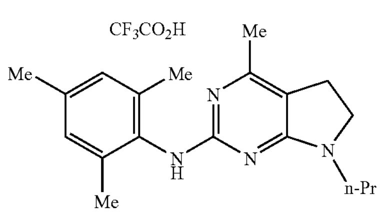 | (4-Methyl-7-propyl-6,7-dihydro-5H-pyrrolo[2,3-d]pyrimidin-2-yl)-(2,4,6-trimethyl-phenyl)-amine; compound with trifluoro-acetic acid | | 311.4<br>311 |
| 32 | 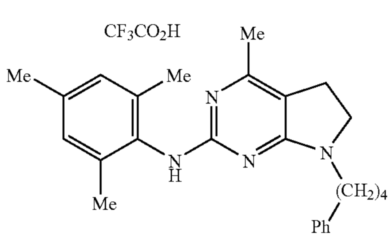 | [4-Methyl-7-(4-phenyl-butyl)-6,7-dihydro-5H-pyrrolo[2,3-d]pyrimidin-2-yl]-(2,4,6-trimethyl-phenyl)-amine; compound with trifluoro-acetic acid | | 401.6<br>401 |

TABLE 1-continued

| cpd # | Structure | Name | mp (° C.) | [M + H]+ calc'd. observed |
|---|---|---|---|---|
| 33 | 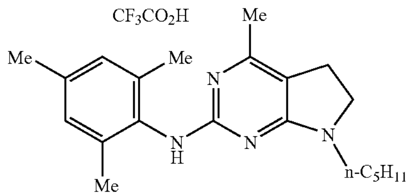 | (4-Methyl-7-pentyl-6,7-dihydro-5H-pyrrolo[2,3-d]pyrimidin-2-yl)-(2,4,6-trimethyl-phenyl)-amine; compound with trifluoro-acetic acid | | 339.5 339 |
| 34 | 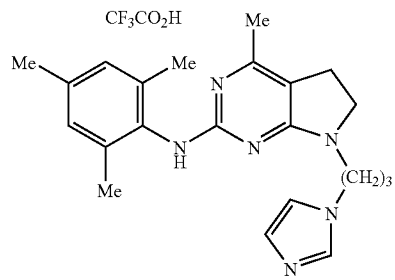 | [7-(3-Imidazol-1-yl-propyl)-4-methyl-6,7-dihydro-5H-pyrrolo[2,3-d]pyrimidin-2-yl]-(2,4,6-trimethyl-phenyl)-amine; compound with trifluoro-acetic acid | | 377.5 377 |
| 35 | 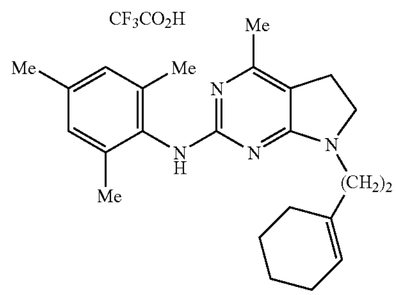 | [7-(2-Cyclohex-1-enyl-ethyl)-4-methyl-6,7-dihydro-5H-pyrrolo[2,3-d]pyrimidin-2-yl]-(2,4,6-trimethyl-phenyl)-amine; compound with trifluoro-acetic acid | | 377.5 377 |
| 36 | 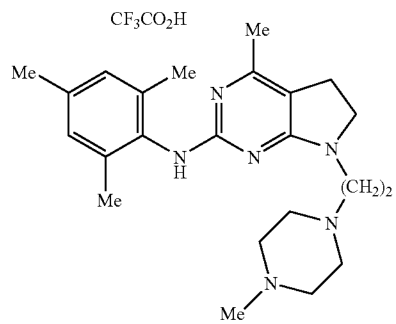 | {4-Methyl-7-[3-(4-methyl-piperazin-1-yl)-propyl]-6,7-dihydro-5H-pyrrolo[2,3-d]pyrimidin-2-yl}-(2,4,6-trimethyl-phenyl)-amine; compound with trifluoro-acetic acid | | 409.6 409 |
| 37 | 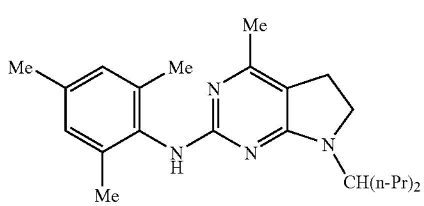 | [4-Methyl-7-(1-propyl-butyl)-6,7-dihydro-5H-pyrrolo[2,3-d]pyrimidin-2-yl]-(2,4,6-trimethyl-phenyl)-amine | | 367.6 367 |
| 38 | 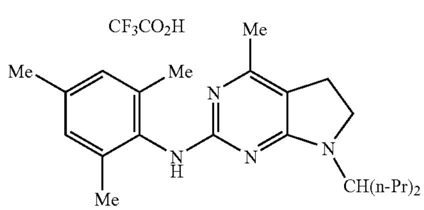 | [4-Methyl-7-(1-propyl-butyl)-6,7-dihydro-5H-pyrrolo[2,3-d]pyrimidin-2-yl]-(2,4,6-trimethyl-phenyl)-amine; compound with trifluoro-acetic acid | | 367.6 367 |

TABLE 1-continued

| cpd # | Structure | Name | mp (° C.) | [M + H]+ calc'd. observed |
|---|---|---|---|---|
| 39 | 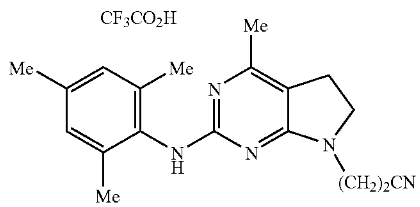 | 3-[4-Methyl-2-(2,4,6-trimethyl-phenyl-amino)-5,6-dihydro-pyrrolo[2,3-d]pyrimidin-7-yl]-propionitrile; compound with trilfuoro-acetic acid | | 322.4 322 |
| 40 | 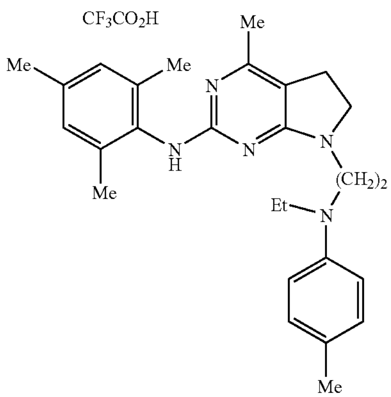 | {7-[2-(Ethyl-p-tolyl-amino)-ethyl]-4-methyl-6,7-dihydro-5H-pyrrolo[2,3-d]pyrimidin-2-yl}-(2,4,6-trimethyl-phenyl)-amine; compound with trifluoro-acetic acid | | 430.6 430 |
| 41 | 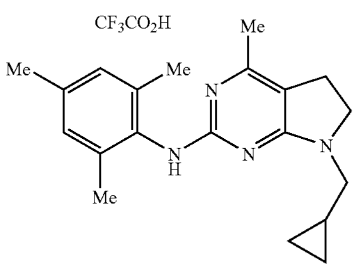 | (7-Cyclopropylmethyl-4-methyl-6,7-dihydro-5H-pyrrolo[2,3-d]pyrimidin-2-yl)-(2,4,6-trimethyl-phenyl)-amine; compound with trifluoro-acetic acid | | 323.5 323 |
| 42 | 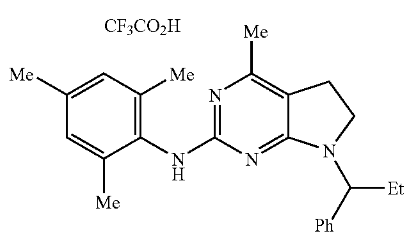 | [4-Methyl-7-(1-phenyl-propyl)-6,7-dihydro-5H-pyrrolo[2,3-d]pyrimidin-2-yl]-(2,4,6-trimethyl-phenyl)-amine; compound with trifluoro-acetic acid | | 387.5 387 |
| 43 | 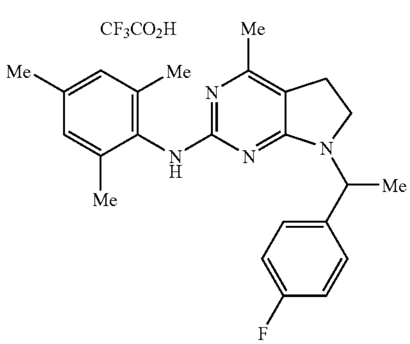 | {7-[1-(4-Fluoro-phenyl)-ethyl]-4-methyl-6,7-dihydro-5H-pyrrolo[2,3-d]pyrimidin-2-yl}-(2,4,6-trimethyl-phenyl)-amine; compound with trifluoro-acetic acid | | 391.5 391 |

TABLE 1-continued

| cpd # | Structure | Name | mp (° C.) | [M + H]+ calc'd. observed |
|---|---|---|---|---|
| 44 | CF₃CO₂H | [4-Methyl-7-(2-thiophen-2-yl-ethyl)-6,7-dihydro-5H-pyrrolo[2,3-d]pyrimidin-2-yl]-(2,4,6-trimethyl-phenyl)-amine; compound with trifluoro-acetic acid | | 379.5 379 |
| 45 | CF₃CO₂H | [7-(2,4-Dichloro-6-methyl-benzyl)-4-methyl-6,7-dihydro-5H-pyrrolo[2,3-d]pyrimidin-2-yl]-(2,4,6-trimethyl-phenyl)-amine; compound with trifluoro-acetic acid | | 441.4 441 |
| 46 | CF₃CO₂H | [4-Methyl-7-(2-phenoxy-ethyl)-6,7-dihydro-5H-pyrrolo[2,3-d]pyrimidin-2-yl]-(2,4,6-trimethyl-phenyl)-amine; compound with trifluoro-acetic acid | | 389.5 389 |
| 47 | CF₃CO₂H | [7-(1-Benzyl-pyrrolidin-3-yl)-4-methyl-6,7-dihydro-5H-pyrrolo[2,3-d]pyrimidin-2-yl]-(2,4,6-trimethyl-phenyl)-amine; compound with trifluoro-acetic acid | | 428.6 428 |
| 48 | CF₃CO₂H | 1-[4-Methyl-2-(2,4,6-trimethyl-phenyl-amino)-5,6-dihydro-pyrrolo[2,3-d]pyrimidin-7-yl]-butan-2-ol; compound with trifluoro-acetic acid | | 341.5 341 |

TABLE 1-continued

| cpd # | Structure | Name | mp (° C.) | [M + H]+ calc'd. observed |
|---|---|---|---|---|
| 49 | CF₃CO₂H, mesityl-NH-pyrrolo[2,3-d]pyrimidine with 4-hydroxycyclohexyl | 4-[4-Methyl-2-(2,4,6-trimethyl-phenyl-amino)-5,6-dihydro-pyrrolo[2,3-d]pyrimidin-7-yl]-cyclohexanol; compound with trifluoro-acetic acid | | 367.5 367 |
| 50 | CF₃CO₂H, mesityl-NH-pyrrolo[2,3-d]pyrimidine with adamantyl | (7-Adamantan-1-yl-4-methyl-6,7-dihydro-5H-pyrrolo[2,3-d]pyrimidin-2-yl)-(2,4,6-trimethyl-phenyl)-amine; compound with trifluoro-acetic acid | | 403.6 403 |
| 51 | CF₃CO₂H, mesityl-NH-pyrrolo[2,3-d]pyrimidine with 3-fluorophenethyl | {7-[2-(3-Fluoro-phenyl)-ethyl]-4-methyl-6,7-dihydro-5H-pyrrolo[2,3-d]pyrimidin-2-yl}-(2,4,6-trimethyl-phenyl)-amine; compound with trifluoro-acetic acid | | 391.5 391 |
| 52 | CF₃CO₂H, mesityl-NH-pyrrolo[2,3-d]pyrimidine with indan-2-yl | (7-Indan-2-yl-4-methyl-6,7-dihydro-5H-pyrrolo[2,3-d]pyrimidin-2-yl)-(2,4,6-trimethyl-phenyl)-amine; compound with trifluoro-acetic acid | | 385.5 385 |
| 53 | CF₃CO₂H, mesityl-NH-pyrrolo[2,3-d]pyrimidine with 2-(4-fluorophenyl)-1,1-dimethylethyl | {7-[2-(4-Fluoro-phenyl)-1,1-dimethyl-ethyl]-4-methyl-6,7-dihydro-5H-pyrrolo[2,3-d]pyrimidin-2-yl}-(2,4,6-trimethyl-phenyl)-amine; compound with trifluoro-acetic acid | | 419.6 419 |

TABLE 1-continued

| cpd # | Structure | Name | mp (° C.) | [M + H]+ calc'd. observed |
|---|---|---|---|---|
| 54 | CF₃CO₂H; mesityl-NH-[4-methyl-pyrrolo[2,3-d]pyrimidin-2-yl], N7-(CH₂)₃O-n-Pr | [4-Methyl-7-(3-propoxy-propyl)-6,7-dihydro-5H-pyrrolo[2,3-d]pyrimidin-2-yl]-(2,4,6-trimethyl-phenyl)-amine; compound with trifluoro-acetic acid | | 369.5<br>369 |
| 55 | CF₃CO₂H; mesityl-NH-[4-methyl-pyrrolo[2,3-d]pyrimidin-2-yl], N7-CH₂-(1,3-dioxolan-2-yl) | [7-(2-[1,3]Dioxolan-2-yl-ethyl)-4-methyl-6,7-dihydro-5H-pyrrolo[2,3-d]pyrimidin-2-yl]-(2,4,6-trimethyl-phenyl)-amine; compound with trifluoro-acetic acid | | 369.5<br>369 |
| 56 | CF₃CO₂H; mesityl-NH-[4-methyl-pyrrolo[2,3-d]pyrimidin-2-yl], N7-CH(Ph)(CH₂)₂OH | 3-[4-Methyl-2-(2,4,6-trimethyl-phenyl-amino)-5,6-dihydro-pyrrolo[2,3-d]pyrimidin-7-yl]-3-phenyl-propan-1-ol; compound with trifluoro-acetic acid | | 403.5<br>403 |
| 57 | CF₃CO₂H; mesityl-NH-[4-methyl-pyrrolo[2,3-d]pyrimidin-2-yl], N7-CH₂-(5-methyl-pyrazin-2-yl) | [4-Methyl-7-(5-methyl-pyrazin-2-ylmethyl)-6,7-dihydro-5H-pyrrolo[2,3-d]pyrimidin-2-yl]-(2,4,6-trimethyl-phenyl)-amine; compound with trifluoro-acetic acid | | 375.5<br>375 |
| 58 | CF₃CO₂H; mesityl-NH-[4-methyl-pyrrolo[2,3-d]pyrimidin-2-yl], N7-(CH₂)₂-(1-benzyl-piperidin-4-yl) | {7-[2-(1-Benzyl-piperidin-4-yl)-ethyl]-4-methyl-6,7-dihydro-5H-pyrrolo[2,3-d]pyrimidin-2-yl}-(2,4,6-trimethyl-phenyl)-amine; compound with trifluoro-acetic acid | | 470.7<br>470 |

TABLE 1-continued

| cpd # | Structure | Name | mp (° C.) | [M + H]+ calc'd. observed |
|---|---|---|---|---|
| 59 | CF3CO2H, mesityl-NH-pyrrolopyrimidine with 2-(1H-indol-3-yl)ethyl on N7 | {7-[2-(1H-Indol-3-yl)-ethyl]-4-methyl-6,7-dihydro-5H-pyrrolo[2,3-d]pyrimidin-2-yl}-(2,4,6-trimethyl-phenyl)-amine; compound with trifluoro-acetic acid | | 412.6 412 |
| 60 | CF3CO2H, mesityl-NH-pyrrolopyrimidine with Ph on N7 | (4-Methyl-7-phenyl-6,7-dihydro-5H-pyrrolo[2,3-d]pyrimidin-2-yl)-(2,4,6-trimethyl-phenyl)-amine; compound with trifluoro-acetic acid | | 345.5 345 |
| 61 | CF3CO2H, mesityl-NH-pyrrolopyrimidine with 2,4-dimethylphenyl on N7 | [7-(2,4-Dimethyl-phenyl)-4-methyl-6,7-dihydro-5H-pyrrolo[2,3-d]pyrimidin-2-yl]-(2,4,6-trimethyl-phenyl)-amine; compound with trifluoro-acetic acid | | 373.5 373 |
| 62 | CF3CO2H, mesityl-NH-pyrrolopyrimidine with azepan-2-on-3-yl on N7 | 3-[4-Methyl-2-(2,4,6-trimethyl-phenylamino)-5,6-dihydro-pyrrolo[2,3-d]pyrimidin-7-yl]-azepan-2-one; compound with trifluoro-acetic acid | | 380.5 380 |
| 63 | CF3CO2H, mesityl-NH-pyrrolopyrimidine with 2-(3H-imidazol-4-yl)ethyl on N7 | {7-[2-(3H-Imidazol-4-yl)-ethyl]-4-methyl-6,7-dihydro-5H-pyrrolo[2,3-d]pyrimidin-2-yl}-(2,4,6-trimethyl-phenyl)-amine; compound with trifluoro-acetic acid | | 363.5 363 |

TABLE 1-continued

| cpd # | Structure | Name | mp (° C.) | [M + H]+ calc'd. observed |
|---|---|---|---|---|
| 64 | 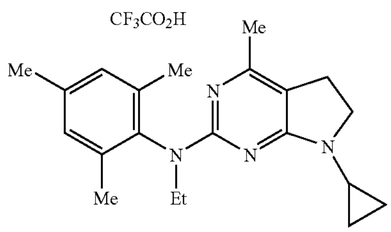 | (7-Cyclopropyl-4-methyl-6,7-di-hydro-5H-pyrrolo[2,3-d]pyrimidin-2-yl)-ethyl-(2,4,6-tri-methyl-phenyl)-amine; compound with trifluoro-acetic acid | | 337.5 337 |
| 65 | 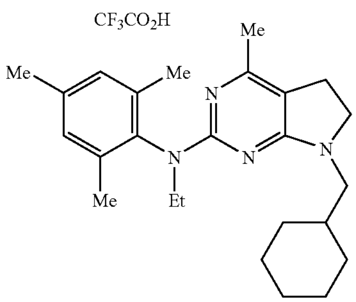 | (7-Cyclohexylmethyl-4-methyl-6,7-di-hydro-5H-pyrrolo[2,3-d]pyrimidin-2-yl)-ethyl-(2,4,6-tri-methyl-phenyl)-amine; compound with trifluoro-acetic acid | | 393.6 393 |
| 66 | 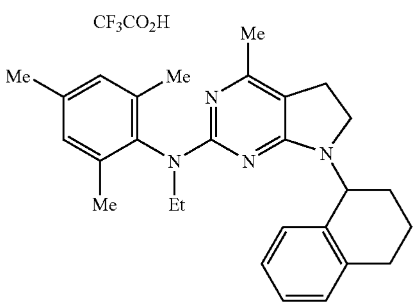 | Ethyl-[4-methyl-7-(1,2,3,4-tetra-hydro-naphthalen-1-yl)-6,7-di-hydro-5H-pyrrolo[2,3-d]pyrimidin-2-yl]-(2,4,6-tri-methyl-phenyl)-amine; compound with trifluoro-acetic acid | | 427.6 427 |
| 67 | 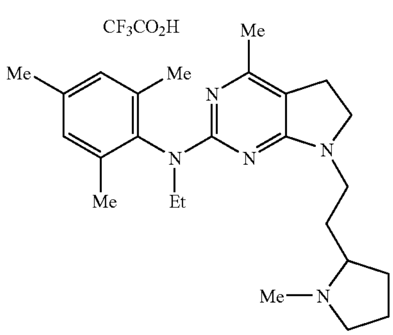 | Ethyl-{4-methyl-7-[2-(1-methyl-pyrrolidin-2-yl)-ethyl]-6,7-di-hydro-5H-pyrrolo[2,3-d]pyrimidin-2-yl}-(2,4,6-tri-methyl-phenyl)-amine; compound with trifluoro-acetic acid | | 408.6 408 |
| 68 | 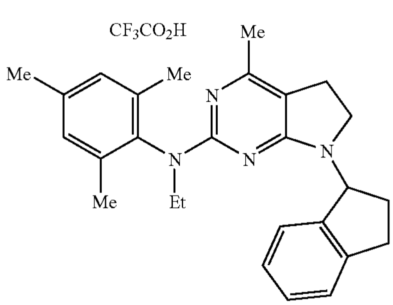 | Ethyl-(7-indan-1-yl-4-methyl-6,7-di-hydro-5H-pyrrolo[2,3-d]pyrimidin-2-yl)-(2,4,6-tri-methyl-phenyl)-amine; compound with trifluoro-acetic acid | | 413.6 413 |

TABLE 1-continued

| cpd # | Structure | Name | mp (° C.) | [M + H]+ calc'd. observed |
|---|---|---|---|---|
| 69 | 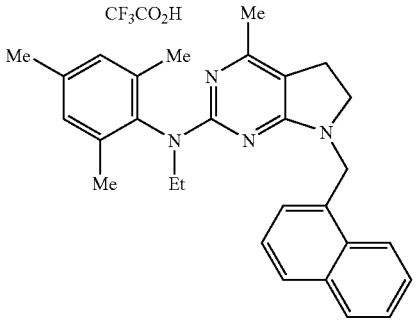 | Ethyl-(4-methyl-7-naphthalen-1-yl-methyl-6,7-dihydro-5H-pyrrolo[2,3-d]pyrimdin-2-yl)-(2,4,6-trimethyl-phenyl)-amine; compound with trifluoro-acetic acid | | 437.6 437 |
| 70 | 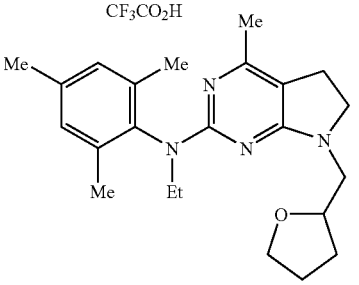 | Ethyl-[4-methyl-7-(tetrahydro-furan-2-ylmethyl)-6,7-dihydro-5H-pyrrolo[2,3-d]pyrimidin-2-yl]-(2,4,6-trimethyl-phenyl)-amine; compound with trifluoro-acetic acid | | 381.5 381 |
| 71 | 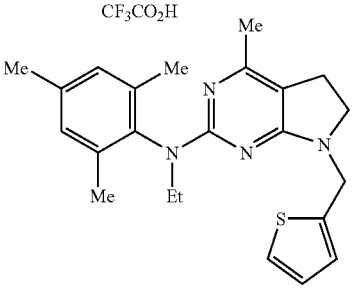 | Ethyl-(4-methyl-7-thiophen-2-yl-methyl-6,7-dihydro-5H-pyrrolo[2,3-d]pyrimidin-2-yl)-(2,4,6-trimethyl-phenyl)-amine; compound with trifluoro-acetic acid | | 393.6 393 |
| 72 | 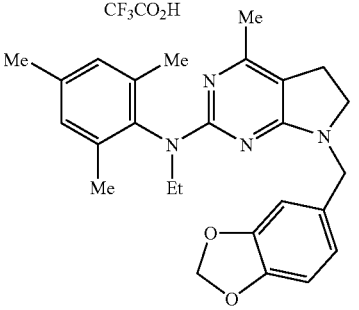 | (7-Benzo[1,3]dioxol-5-ylmethyl-4-methyl-6,7-dihydro-5H-pyrrolo[2,3-d]pyrimidin-2-yl)-ethyl-(2,4,6-trimethyl-phenyl)-amine; compound with trifluoro-acetic acid | | 431.5 431 |

TABLE 1-continued

| cpd # | Structure | Name | mp (° C.) | [M + H]+ calc'd. observed |
|---|---|---|---|---|
| 73 | 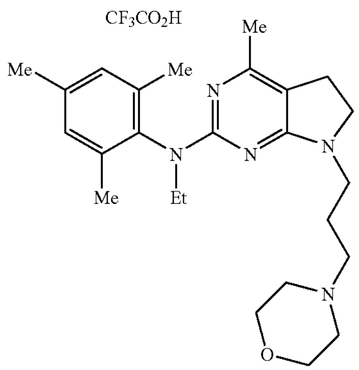 | Ethyl-[4-methyl-7-(3-morpholin-4-yl-propyl)-6,7-dihydro-5H-pyrrolo[2,3-d]pyrimidin-2-yl]-(2,4,6-trimethyl-phenyl)-amine; compound with trifluoro-acetic acid | | 424.6 424 |
| 74 | 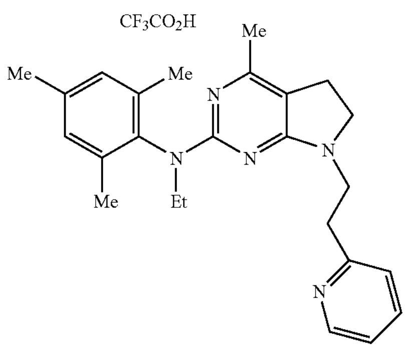 | Ethyl-[4-methyl-7-(2-pyridin-2-yl-ethyl)-6,7-dihydro-5H-pyrrolo[2,3-d]pyrimidin-2-yl]-(2,4,6-trimethyl-phenyl)-amine; compound with trifluoro-acetic acid | | 402.6 402 |
| 75 | 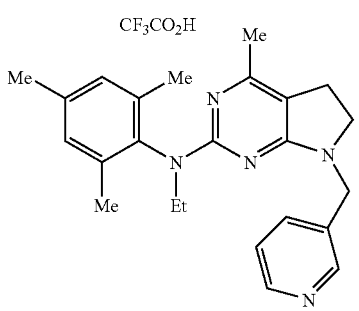 | Ethyl-(4-methyl-7-pyridin-3-yl-methyl-6,7-dihydro-5H-pyrrolo[2,3-d]pyrimidin-2-yl)-(2,4,6-trimethyl-phenyl)-amine; compound with trifluoro-acetic acid | | 388.5 388 |
| 76 | 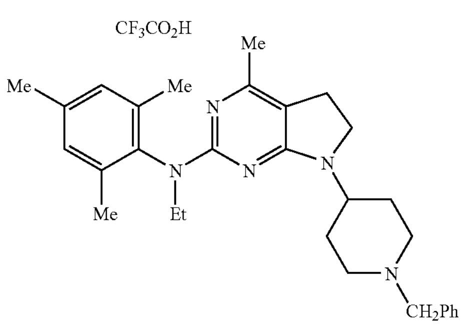 | [7-(1-Benzyl-piperidin-4-yl)-4-methyl-6,7-dihydro-5H-pyrrolo[2,3-d]pyrimidin-2-yl]-ethyl-(2,4,6-trimethyl-phenyl)-amine; compound with trifluoro-acetic acid | | 470.7 470 |

TABLE 1-continued

| cpd # | Structure | Name | mp (° C.) | [M + H]+ calc'd. observed |
|---|---|---|---|---|
| 77 | 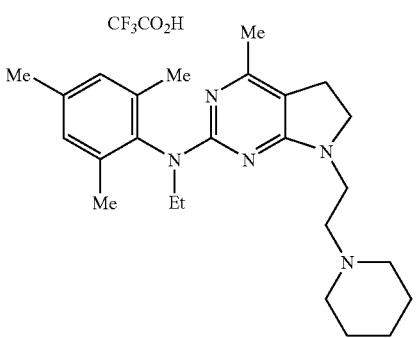 | Ethyl-[4-methyl-7-(2-piperidin-1-yl-ethyl)-6,7-dihydro-5H-pyrrolo[2,3-d]pyrimdin-2-yl]-(2,4,6-trimethyl-phenyl)-amine; compound with trifluoro-acetic acid | | 408.6 408 |
| 78 | 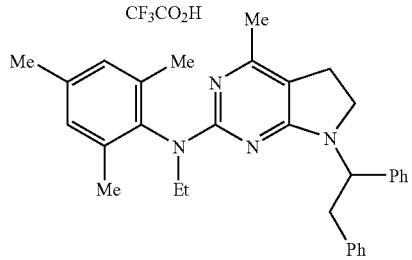 | [7-(1,2-Diphenyl-ethyl)-4-methyl-6,7-dihydro-5H-pyrrolo[2,3-d]pyrimidin-2-yl]-ethyl-(2,4,6-trimethyl-phenyl)-amine; compound with trifluoro-acetic acid | | 477.7 477 |
| 79 | 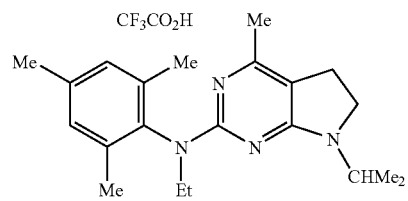 | Ethyl-(7-isopropyl-4-methyl-6,7-dihydro-5H-pyrrolo[2,3-d]pyrimidin-2-yl)-(2,4,6-trimethyl-phenyl)-amine; compound with trifluoro-acetic acid | | 339.5 339 |
| 80 | 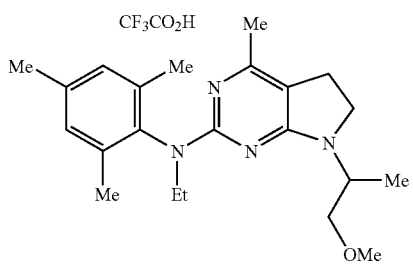 | Ethyl-[7-(2-methoxy-1-methyl-ethyl)-4-methyl-6,7-dihydro-5H-pyrrolo[2,3-d]pyrimidin-2-yl]-(2,4,6-trimethyl-phenyl)-amine; compound with trifluoro-acetic acid | | 369.5 369 |
| 81 | 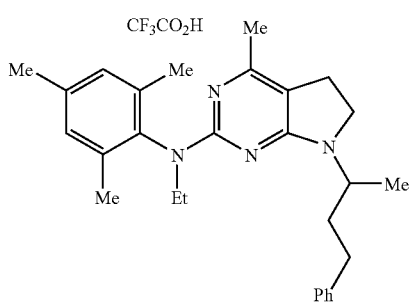 | Ethyl-[4-methyl-7-(1-methyl-3-phenyl-propyl)-6,7-dihydro-5H-pyrrolo[2,3-d]pyrimidin-2-yl]-(2,4,6-trimethyl-phenyl)-amine; compound with trifluoro-acetic acid | | 429.6 429 |

TABLE 1-continued

| cpd # | Structure | Name | mp (° C.) | [M + H]+ calc'd. observed |
|---|---|---|---|---|
| 82 | CF₃CO₂H | (7-Benzyl-4-methyl-6,7-dihydro-5H-pyrrolo[2,3-d]pyrimidin-2-yl)-ethyl-(2,4,6-trimethyl-phenyl)-amine; compound with trifluoro-acetic acid | | 387.5<br>387 |
| 83 | CF₃CO₂H | Ethyl-[7-(3-fluoro-benzyl)-4-methyl-6,7-dihydro-5H-pyrrolo[2,3-d]pyrimidin-2-yl]-(2,4,6-trimethyl-phenyl)-amine; compound with trifluoro-acetic acid | | 405.5<br>405 |
| 84 | CF₃CO₂H | [7-(3,4-Dimethoxy-benzyl)-4-methyl-6,7-dihydro-5H-pyrrolo[2,3-d]pyrimidin-2-yl]-ethyl-(2,4,6-trimethyl-phenyl)-amine; compound with trifluoro-acetic acid | | 447.6<br>447 |
| 85 | CF₃CO₂H | Ethyl-(4-methyl-7-phenethyl-6,7-dihydro-5H-pyrrolo[2,3-d]pyrimidin-2-yl)-(2,4,6-trimethyl-phenyl)-amine; compound with trifluoro-acetic acid | | 401.6<br>401 |
| 86 | CF₃CO₂H | (7-Allyl-4-methyl-6,7-dihydro-5H-pyrrolo[2,3-d]pyrimidin-2-yl)-ethyl-(2,4,6-trimethyl-phenyl)-amine; compound with trifluoro-acetic acid | | 337.5<br>337 |

TABLE 1-continued

| cpd # | Structure | Name | mp (° C.) | [M + H]+ calc'd. observed |
|---|---|---|---|---|
| 87 | 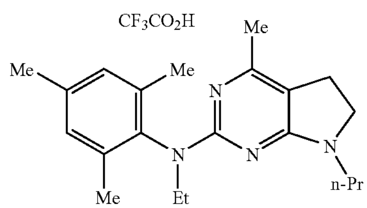 | Ethyl-(4-methyl-7-propyl-6,7-dihydro-5H-pyrrolo[2,3-d]pyrimidin-2-yl)-(2,4,6-trimethyl-phenyl)-amine; compound with trifluoro-acetic acid | | 339.5 339 |
| 88 | 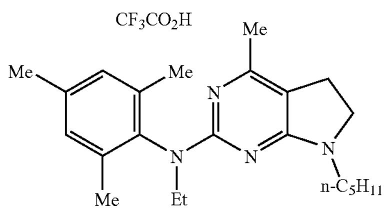 | Ethyl-(4-methyl-7-pentyl-6,7-dihydro-5H-pyrrolo[2,3-d]pyrimidin-2-yl)-(2,4,6-trimethyl-phenyl)-amine; compound with trifluoro-acetic acid | | 367.6 367 |
| 89 | 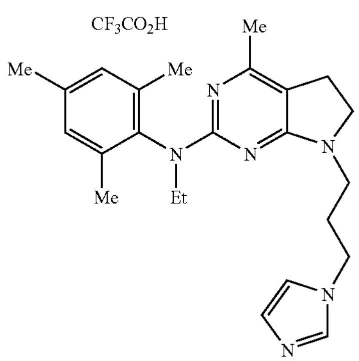 | Ethyl-[7-(3-imidazol-1-yl-propyl)-4-methyl-6,7-dihydro-5H-pyrrolo[2,3-d]pyrimidin-2-yl]-(2,4,6-trimethyl-phenyl)-amine; compound with trifluoro-acetic acid | | 405.6 405 |
| 90 | 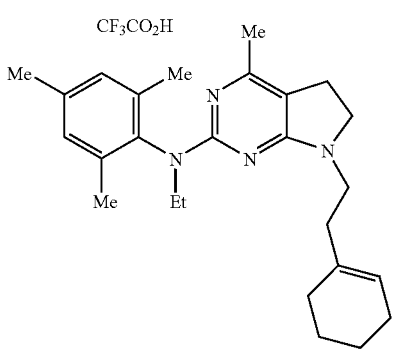 | [7-(2-Cyclohex-1-enyl-ethyl)-4-methyl-6,7-dihydro-5H-pyrrolo[2,3-d]pyrimidin-2-yl]-ethyl-(2,4,6-trimethyl-phenyl)-amine; compound with trifluoro-acetic acid | | 405.6 405 |
| 91 | 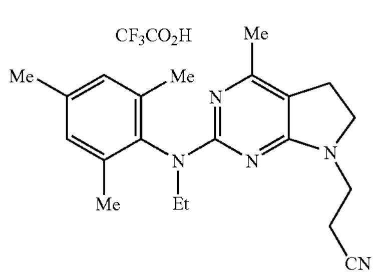 | 3-{2-[Ethyl-(2,4,6-trimethyl-phenyl)-amino]-4-methyl-5,6-dihydro-pyrrolo[2,3-d]pyrimidin-7-yl}-propionitrile; compound with trifluoro-acetic acid | | 350.5 350 |

TABLE 1-continued

| cpd # | Structure | Name | mp (° C.) | [M + H]+ calc'd. observed |
|---|---|---|---|---|
| 92 | 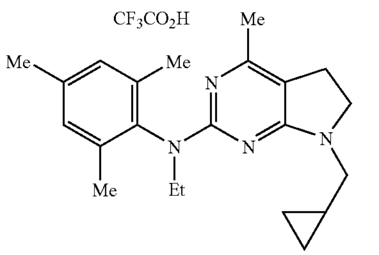 | (7-Cyclopropylmethyl-4-methyl-6,7-dihydro-5H-pyrrolo[2,3-d]pyrimidin-2-yl)-ethyl-(2,4,6-trimethyl-phenyl)-amine; compound with trifluoro-acetic acid | | 351.5 351 |
| 93 | 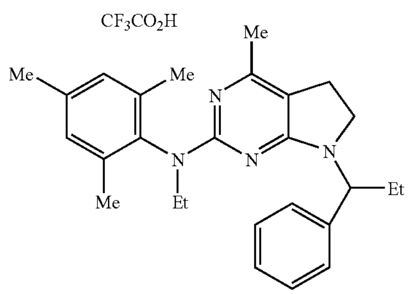 | Ethyl-[4-methyl-7-(1-phenyl-propyl)-6,7-dihydro-5H-pyrrolo[2,3-d]pyrimidin-2-yl]-(2,4,6-trimethyl-phenyl)-amine; compound with trifluoro-acetic acid | | 415.6 415 |
| 94 | 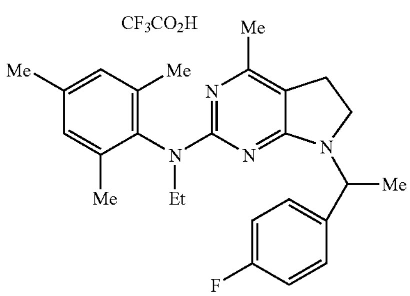 | Ethyl-{7-[1-(4-fluoro-phenyl)-ethyl]-4-methyl-6,7-dihydro-5H-pyrrolo[2,3-d]pyrimidin-2-yl}-(2,4,6-trimethyl-phenyl)-amine; compound with trifluoro-acetic acid | | 419.6 419 |
| 95 | 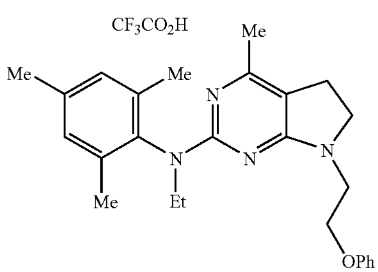 | Ethyl-[4-methyl-7-(2-phenoxy-ethyl)-6,7-dihydro-5H-pyrrolo[2,3-d]pyrimidin-2-yl]-(2,4,6-trimethyl-phenyl)-amine; compound with trifluoro-acetic acid | | 417.6 417 |
| 96 | 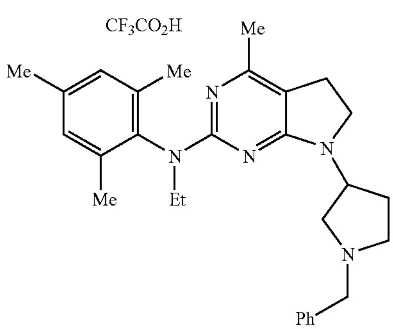 | [7-(1-Benzyl-pyrrolidin-3-yl)-4-methyl-6,7-dihydro-5H-pyrrolo[2,3-d]pyrimidin-2-yl]-ethyl-(2,4,6-trimethyl-phenyl)-amine; compound with trifluoro-acetic acid | | 456.6 456 |

TABLE 1-continued

| cpd # | Structure | Name | mp (° C.) | [M + H]+ calc'd. observed |
|---|---|---|---|---|
| 97 | CF₃CO₂H | Ethyl-{7-[2-(3-fluoro-phenyl)-ethyl]-4-methyl-6,7-dihydro-5H-pyrrolo[2,3-d]pyrimidin-2-yl}-(2,4,6-trimethyl-phenyl)-amine; compound with trifluoro-acetic acid | | 419.6 419 |
| 98 | CF₃CO₂H | Ethyl-[4-methyl-7-(3-propoxy-propyl)-6,7-dihydro-5H-pyrrolo[2,3-d]pyrimidin-2-yl]-(2,4,6-trimethyl-phenyl)-amine; compound with trifluoro-acetic acid | | 397.6 397 |
| 99 | CF₃CO₂H | [7-(2-[1,3]Dioxolan-2-yl-ethyl)-4-methyl-6,7-dihydro-5H-pyrrolo[2,3-d]pyrimidin-2-yl]-ethyl-(2,4,6-trimethyl-phenyl)-amine; compound with trifluoro-acetic acid | | 397.5 397 |
| 100 | CF₃CO₂H | Ethyl-[4-methyl-7-(5-methyl-pyrazin-2-ylmethyl)-6,7-dihydro-5H-pyrrolo[2,3-d]pyrimidin-2-yl]-(2,4,6-trimethyl-phenyl)-amine; compound with trifluoro-acetic acid | | 403.5 403 |
| 101 | CF₃CO₂H | {7-[2-(1-Benzyl-piperidin-4-yl)-ethyl]-4-methyl-6,7-dihydro-5H-pyrrolo[2,3-d]pyrimidin-2-yl}-ethyl-(2,4,6-trimethyl-phenyl)-amine; compound with trifluoro-acetic acid | | 498.7 498 |

TABLE 1-continued

| cpd # | Structure | Name | mp (° C.) | [M + H]+ calc'd. observed |
|---|---|---|---|---|
| 102 | 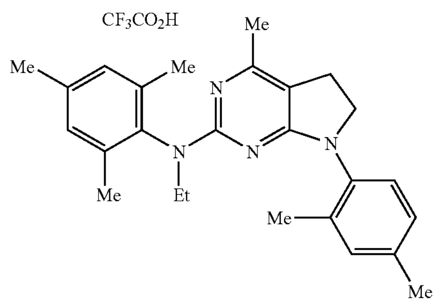 | [7-(2,4-Dimethyl-phenyl)-4-methyl-6,7-dihydro-5H-pyrrolo[2,3-d]pyrimidin-2-yl]-ethyl-(2,4,6-trimethyl-phenyl)-amine; compound with trifluoro-acetic acid | | 401.6 401 |
| 103 | 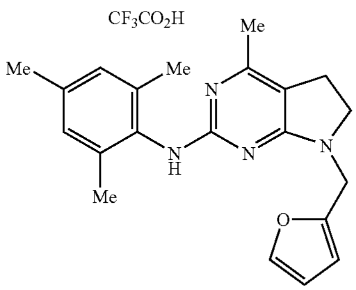 | (7-Furan-2-ylmethyl-4-methyl-6,7-dihydro-5H-pyrrolo[2,3-d]pyrimidin-2-yl)-(2,4,6-trimethyl-phenyl)-amine; compound with trifluoro-acetic acid | | 349.4 349 |
| 104 | 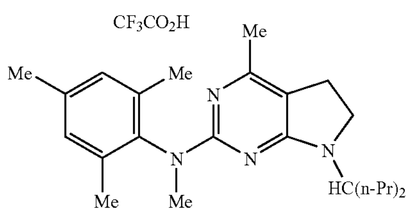 | Methyl-[4-methyl-7-(1-propyl-butyl)-6,7-dihydro-5H-pyrrolo[2,3-d]pyrimidin-2-yl]-(2,4,6-trimethyl-phenyl)-amine; compound with trifluoro-acetic acid | | 381.6 381 |
| 105 | 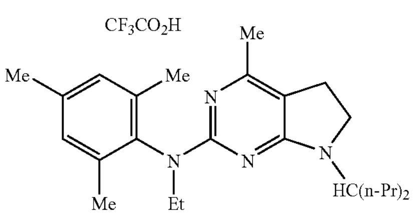 | Ethyl-[4-methyl-7-(1-propyl-butyl)-6,7-dihydro-5H-pyrrolo[2,3-d]pyrimidin-2-yl]-(2,4,6-trimethyl-phenyl)-amine; compound with trifluoro-acetic acid | | 395.6 395 |
| 106 | 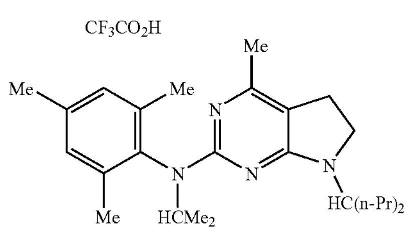 | Isopropyl-[4-methyl-7-(1-propyl-butyl)-6,7-dihydro-5H-pyrrolo[2,3-d]pyrimidin-2-yl]-(2,4,6-trimethyl-phenyl)-amine; compound with trifluoro-acetic acid | | 409.6 409 |
| 107 | 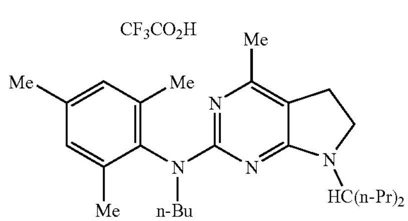 | Butyl-[4-methyl-7-(1-propyl-butyl)-6,7-dihydro-5H-pyrrolo[2,3-d]pyrimidin-2-yl]-(2,4,6-trimethyl-phenyl)-amine; compound with trifluoro-acetic acid | | 423.7 423 |

TABLE 1-continued

| cpd # | Structure | Name | mp (° C.) | [M + H]+ calc'd. observed |
|---|---|---|---|---|
| 108 | 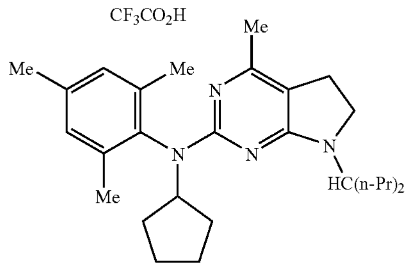 | Cyclopentyl-[4-methyl-7-(1-propyl-butyl)-6,7-dihydro-5H-pyrrolo[2,3-d]pyrimidin-2-yl]-(2,4,6-trimethyl-phenyl)-amine; compound with trifluoro-acetic acid | | 435.7 435 |
| 109 | 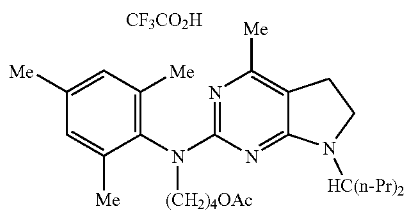 | Acetic acid 4-[[4-methyl-7-(1-propyl-butyl)-6,7-dihydro-5H-pyrrolo[2,3-d]pyrimidin-2-yl]-(2,4,6-trimethyl-phenyl)-amino]-butyl ester; compound with trifluoro-acetic acid | | 481.7 481 |
| 110 | 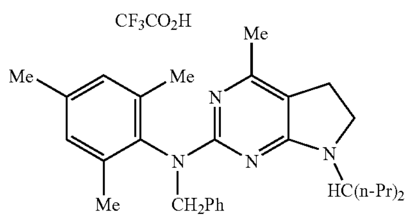 | Benzyl-[4-methyl-7-(1-propyl-butyl)-6,7-dihydro-5H-pyrrolo[2,3-d]pyrimidin-2-yl]-(2,4,6-trimethyl-phenyl)-amine; compound with trifluoro-acetic acid | | 457.7 457 |
| 111 | 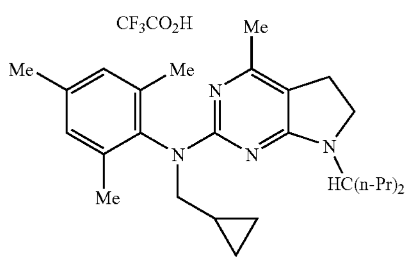 | Cyclopropylmethyl-[4-methyl-7-(1-propyl-butyl)-6,7-dihydro-5H-pyrrolo[2,3-d]pyrimidin-2-yl]-(2,4,6-trimethyl-phenyl)-amine; compound with trifluoro-acetic acid | | 421.6 421 |
| 112 | 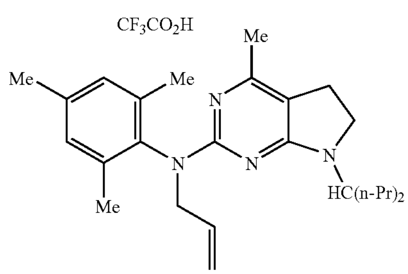 | Allyl-[4-methyl-7-(1-propyl-butyl)-6,7-dihydro-5H-pyrrolo[2,3-d]pyrimidin-2-yl]-(2,4,6-trimethyl-phenyl)-amine; compound with trifluoro-acetic acid | | 407.6 407 |

4-Methyl-5,6,7,8-tetrahydro-pyrido[2,3-d]pyrimidines and 4-methyl-5,8-dihydro-6H-pyrido[2,3-d]pyrimidin-7-ones were prepared as shown in Scheme 2. In step (b) the Principal Synthesis was carried out with diethyl 2-acetyl-glutarate to incorporate a three-carbon carboxylic acid side chain at the 5-position of the pyrimidine XI. After conversion of the 6-hydroxy to a 6-chloro analogue with phosphorus oxychloride in step (c), condensation with a primary amine proceeds to afford a pyrimidone XIII.

In step (e) the lactam was reduction with $BH_3$-THF to afford the corresponding tertiary amine XIV. In addition to $BH_3$-THF, reduction of amides to amines can be carried out with lithium aluminum hydride diisobutylaluminum hydride or other hydride reducing agents. Sodium borohydride is less generally useful. Reductions with hydride reducing agents are usually run in aprotic solvents such as diethyl ether, THF and dimethoxyethane. Catalytic hydrogen also may be utilized for the reduction of amides but high temperature and pressure are typically required. (J. March, supra p.1212-13). In step (f) the amine is optionally substituted by alkylation as described previously.

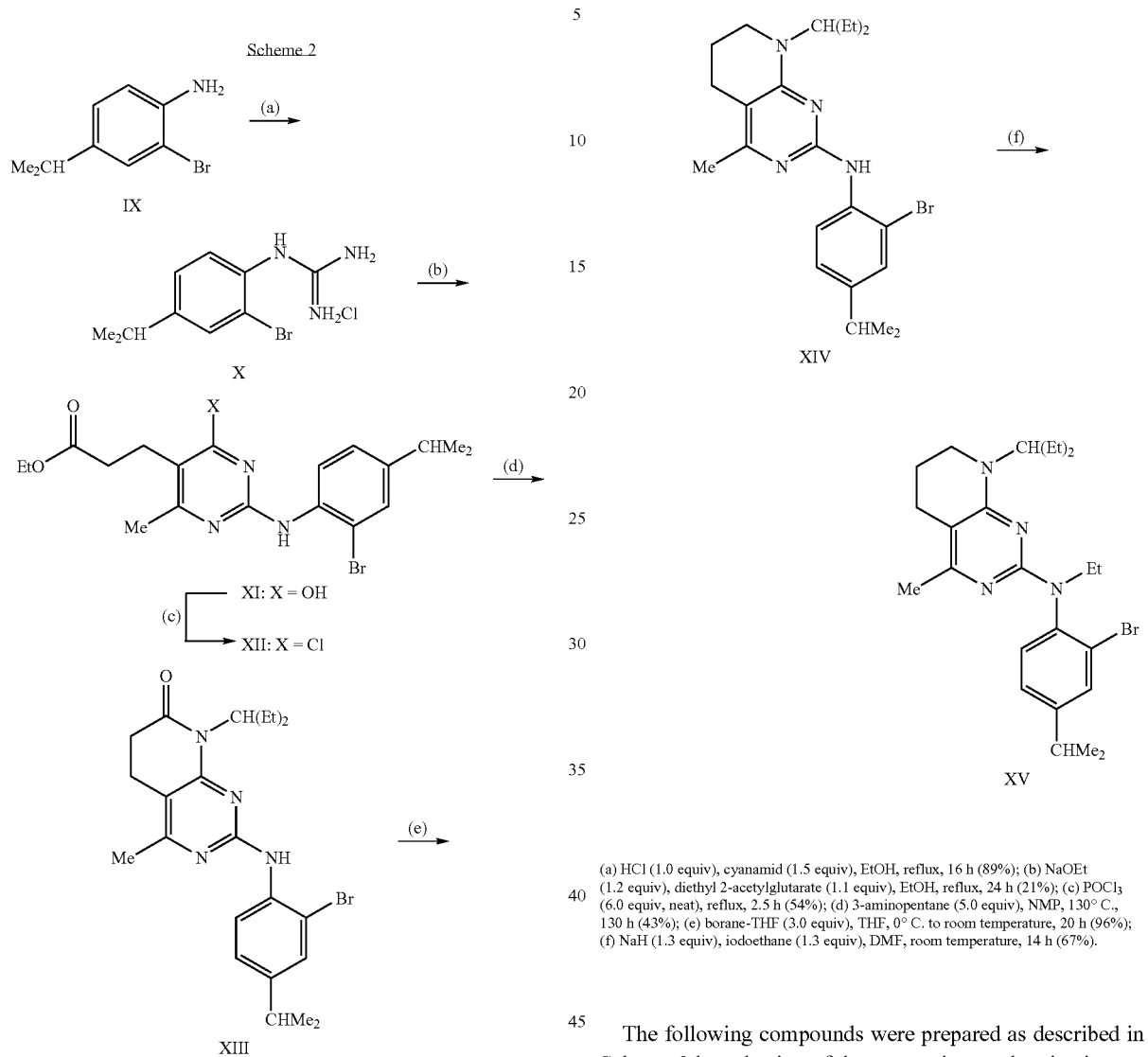

(a) HCl (1.0 equiv), cyanamid (1.5 equiv), EtOH, reflux, 16 h (89%); (b) NaOEt (1.2 equiv), diethyl 2-acetylglutarate (1.1 equiv), EtOH, reflux, 24 h (21%); (c) POCl$_3$ (6.0 equiv, neat), reflux, 2.5 h (54%); (d) 3-aminopentane (5.0 equiv), NMP, 130° C., 130 h (43%); (e) borane-THF (3.0 equiv), THF, 0° C. to room temperature, 20 h (96%); (f) NaH (1.3 equiv), iodoethane (1.3 equiv), DMF, room temperature, 14 h (67%).

The following compounds were prepared as described in Scheme 2 by selection of the appropriate aryl amine in step (a) and the appropriate primary amine in step (f).

TABLE 2

| cpd # | Structure | Name | mp (° C.) | [M + H]$^+$ calc'd. observed |
|---|---|---|---|---|
| 113 | 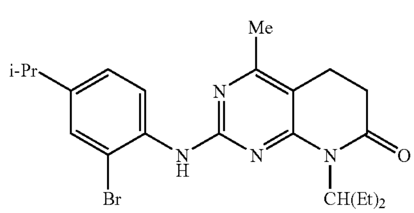 | 2-(2-Bromo-4-isopropyl-phenyl-amino)-8-(1-ethyl-propyl)-4-methyl-5,8-dihydro-6H-pyrido[2,3-d]pyrimidin-7-one | 124-126 | 445.4 445 |

TABLE 2-continued

| cpd # | Structure | Name | mp (° C.) | [M + H]+ calc'd. observed |
|---|---|---|---|---|
| 114 | 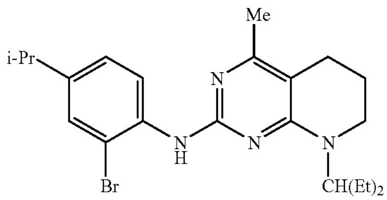 | (2-Bromo-4-isopropyl-phenyl)-[8-(1-ethyl-propyl)-4-methyl-5,6,7,8-tetrahydro-pyrido[2,3-d]pyrimidin-2-yl]-amine | | 431.4 431 |
| 115 | 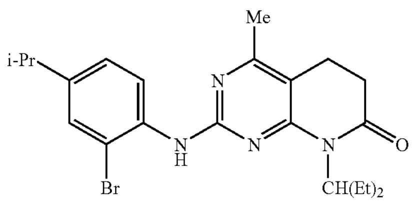 | 2-(2-Bromo-4-isopropyl-phenylamino)-4-methyl-8-(1-propyl-butyl)-5,8-dihydro-6H-pyrido[2,3-d]pyrimidin-7-one | 122-123 | 473.5 473 |
| 116 | 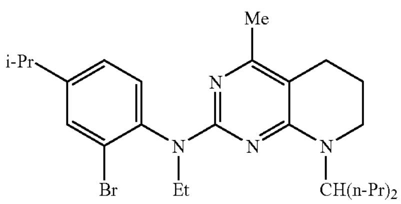 | (2-Bromo-4-isopropyl-phenyl)-ethyl-[8-(1-ethyl-propyl)-4-methyl-5,6,7,8-tetrahydro-pyrido[2,3-d]pyrimidin-2-yl]-amine | | 459.5 459 |
| 117 | 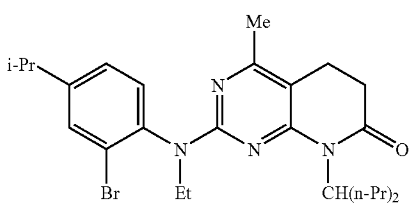 | 2-[(2-Bromo-4-isopropyl-phenyl)-ethyl-amino]-4-methyl-8-(1-propyl-butyl)-5,8-dihydro-6H-pyrido[2,3-d]pyrimidin-7-one | 92-94 | 501.5 501 |
| 118 | 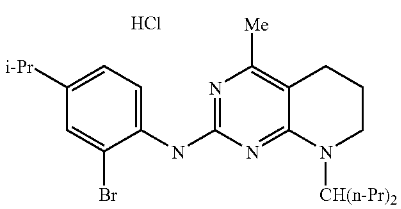 | (2-Bromo-4-isopropyl-phenyl)-[4-methyl-8-(1-propyl-butyl)-5,6,7,8-tetrahydro-pyrido[2,3-d]pyrimidin-2-yl]-amine; compound with hydrogen chloride | 182-184 | 459.5 459 |
| 119 | 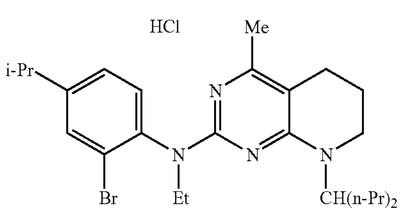 | (2-Bromo-4-isopropyl-phenyl)-ethyl-[4-methyl-8-(1-propyl-butyl)-5,6,7,8-tetrahydro-pyrido[2,3-d]pyrimidin-2-yl]-amine; compound with hydrogen chloride | 201-205 | 487.5 487 |

The trifluoroacetic acid salt of ethyl-(4-methyl-9-thiophen-2-ylmethyl-6,7,8,9-tetrahydro-5H-pyrimido[4,5-b]azepin-2-yl)-(2,4,6-trimethyl-phenyl)-amine was prepared as shown in Scheme 3. In step b) the Principal Synthesis was carried out with 3-acetyl-oxepan-2-one to incorporate a four-carbon side chain at the 5-position of the pyrimidine. Sequential conversion of the side chain and ring hydroxyls to the dichloride was carried out as described in Scheme 1. The cyclization step (d) and optional N-alkylation step (e) were carried out as described in Scheme 1.

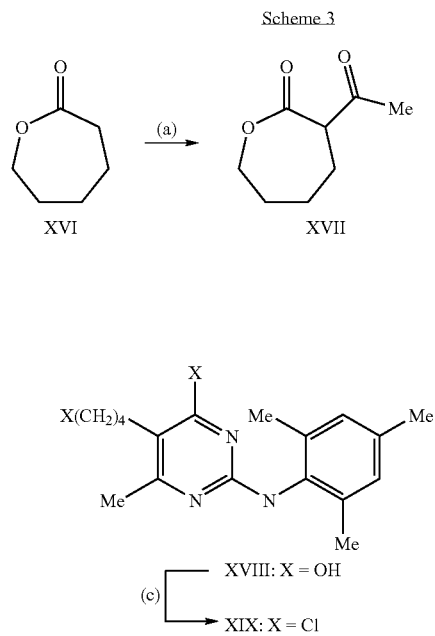

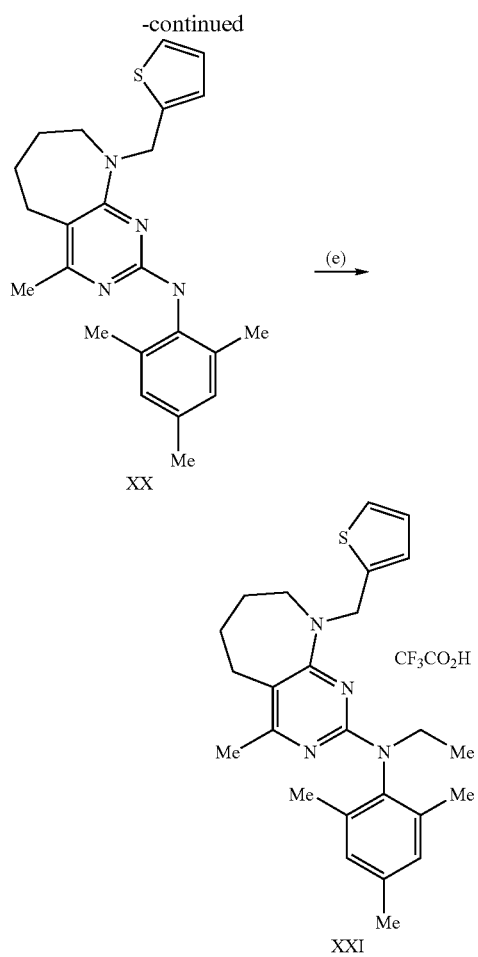

(a) LDA (1.1 equiv), pyruvonitrile (1.1 equiv), -78° C., 10 min (48%); (b) NaOMe (1.15 equiv), IV (1.15 equiv), EtOH—MeOH, reflux, 21 h (46%); (c) POCl₃ (23 equiv, neat), reflux, 17 h (84%); (d) 2-thiophenemethylamine (1.25 equiv), Et₃N (2.5 equiv), NMP, 130° C., 65 h (90%); (e) NaH (1.8 equiv), iodoethane (1.8 equiv), DMF, room temperature, 8 h, then 40° C., 9 h (purified by preparatory RP-HPLC as TFA salt).

TABLE 3

| cpd # | Structure | Name | mp (° C.) | [M + H]⁺ calc'd. observed |
|---|---|---|---|---|
| 120 | 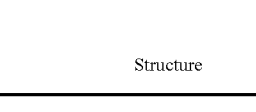 | (9-Cyclohexylmethyl-4-methyl-6,7,8,9-tetrahydro-5H-pyrimido[4,5-b]azepin-2-yl)-ethyl-(2,4,6-trimethyl-phenyl)-amine; compound with trifluoro-acetic acid | | 421.6 421 |

TABLE 3-continued

| cpd # | Structure | Name | mp (° C.) | [M + H]+ calc'd. observed |
|---|---|---|---|---|
| 121 | 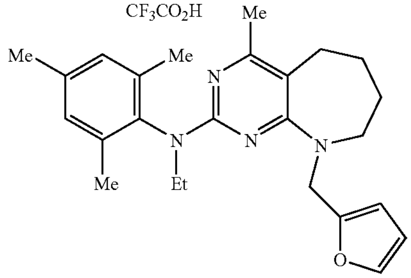 | Ethyl-(9-furan-2-ylmethyl-4-methyl-6,7,8,9-tetrahydro-5H-pyrimido[4,5-b]azepin-2-yl)-(2,4,6-trimethyl-phenyl)-amine; compound with trifluoro-acetic acid | | 405.6 405 |
| 122 | 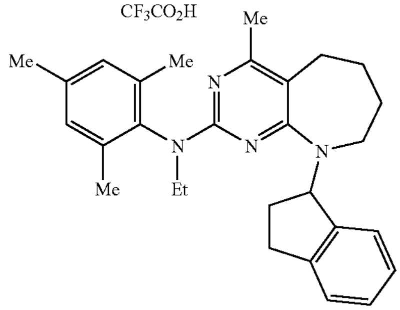 | Ethyl-(9-indan-1-yl-4-methyl-6,7,8,9-tetrahydro-5H-pyrimido[4,5-b]azepin-2-yl)-(2,4,6-trimethyl-phenyl)-amine; compound with trifluoro-acetic acid | | 441.6 441 |
| 123 | 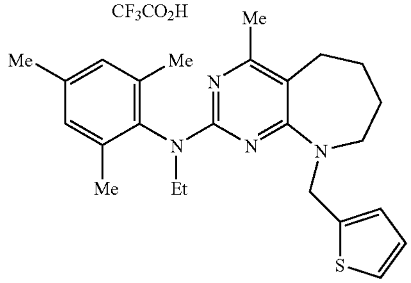 | Ethyl-(4-methyl-9-thiophen-2-ylmethyl-6,7,8,9-tetrahydro-5H-pyrimido[4,5-b]azepin-2-yl)-(2,4,6-trimethyl-phenyl)-amine; compound with trifluoro-acetic acid | | 421.6 421 |
| 124 | 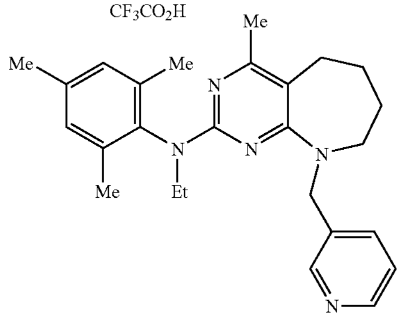 | Ethyl-(4-methyl-9-pyridin-3-ylmethyl-6,7,8,9-tetrahydro-5H-pyrimido[4,5-b]azepin-2-yl)-(2,4,6-trimethyl-phenyl)-amine; compound with trifluoro-acetic acid | | 416.6 416 |
| 125 | 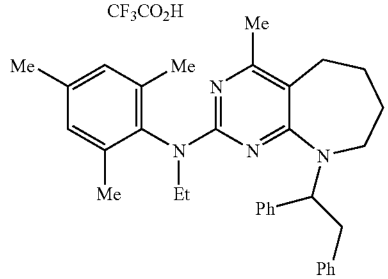 | [9-(1,2-Diphenyl-ethyl)-4-methyl-6,7,8,9-tetrahydro-5H-pyrimido[4,5-b]azepin-2-yl]-ethyl-(2,4,6-trimethyl-phenyl)-amine; compound with trifluoro-acetic acid | | 505.7 505 |

TABLE 3-continued

| cpd # | Structure | Name | mp (° C.) | [M + H]+ calc'd. observed |
|---|---|---|---|---|
| 126 | 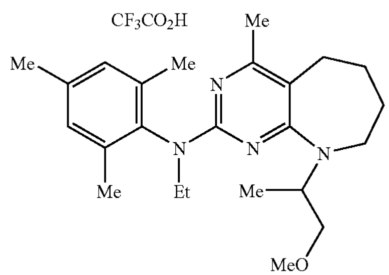 | Ethyl-[9-(2-methoxy-1-methyl-ethyl)-4-methyl-6,7,8,9-tetrahydro-5H-pyrimido[4,5-b]azepin-2-yl]-(2,4,6-trimethyl-phenyl)-amine; compound with trifluoro-acetic acid | | 397.6 397 |
| 127 | 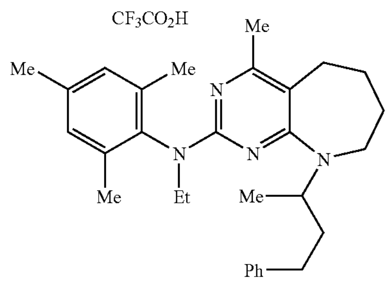 | Ethyl-[4-methyl-9-(1-methyl-3-phenyl-propyl)-6,7,8,9-tetrahydro-5H-pyrimido[4,5-b]azepin-2-yl]-(2,4,6-trimethyl-phenyl)-amine; compound with trifluoro-acetic acid | | 457.7 457 |
| 128 | 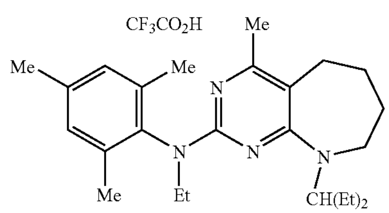 | Ethyl-[9-(1-ethyl-propyl)-4-methyl-6,7,8,9-tetrahydro-5H-pyrimido[4,5-b]azepin-2-yl]-(2,4,6-trimethyl-phenyl)-amine; compound with trifluoro-acetic acid | | 395.6 395 |
| 129 | 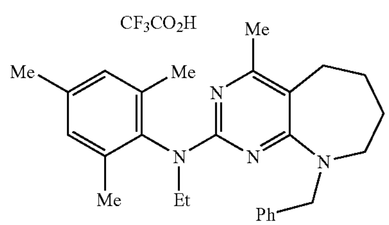 | (9-Benzyl-4-methyl-6,7,8,9-tetrahydro-5H-pyrimido[4,5-b]azepin-2-yl)-ethyl-(2,4,6-trimethyl-phenyl)-amine; compound with trifluoro-acetic acid | | 415.6 415 |
| 130 | 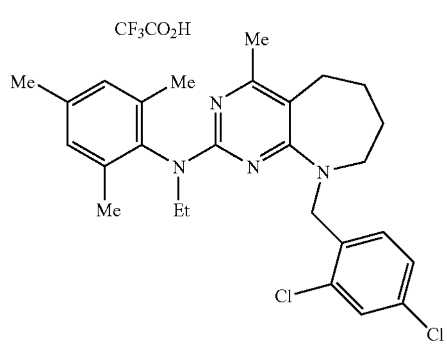 | [9-(2,4-Dichloro-benzyl)-4-methyl-6,7,8,9-tetrahydro-5H-pyrimido[4,5-b]azepin-2-yl]-ethyl-(2,4,6-trimethyl-phenyl)-amine; compound with trifluoro-acetic acid | | 483.5 483 |

TABLE 3-continued

| cpd # | Structure | Name | mp (° C.) | [M + H]+ calc'd. observed |
|---|---|---|---|---|
| 131 | 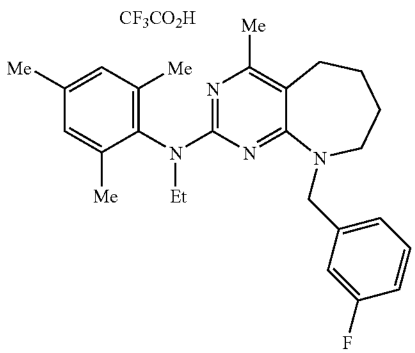 | Ethyl-[9-(3-fluoro-benzyl)-4-methyl-6,7,8,9-tetrahydro-5H-pyrimido[4,5-b]azepin-2-yl]-(2,4,6-trimethyl-phenyl)-amine; compound with trifluoro-acetic acid | | 433.6 433 |
| 132 | 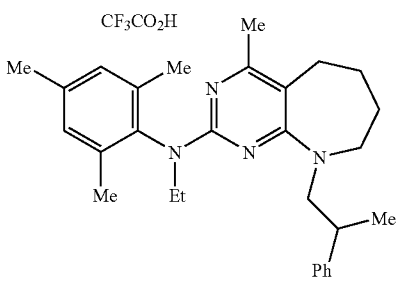 | Ethyl-[4-methyl-9-(2-phenyl-propyl)-6,7,8,9-tetrahydro-5H-pyrimido[4,5-b]azepin-2-yl]-(2,4,6-trimethyl-phenyl)-amine; compound with trifluoro-acetic acid | | 443.6 443 |
| 133 | 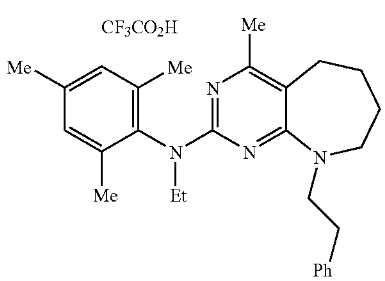 | Ethyl-(4-methyl-9-phenethyl-6,7,8,9-tetrahydro-5H-pyrimido[4,5-b]azepin-2-yl)-(2,4,6-trimethyl-phenyl)-amine; compound with trifluoro-acetic acid | | 429.6 429 |
| 134 | 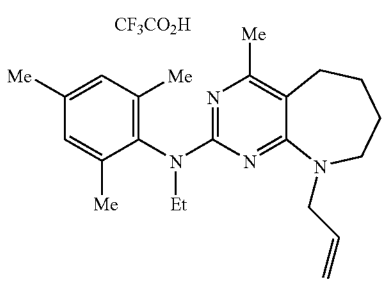 | (9-Allyl-4-methyl-6,7,8,9-tetrahydro-5H-pyrimido[4,5-b]azepin-2-yl)-ethyl-(2,4,6-trimethyl-phenyl)-amine; compound with trifluoro-acetic acid | | 365.5 365 |
| 135 | 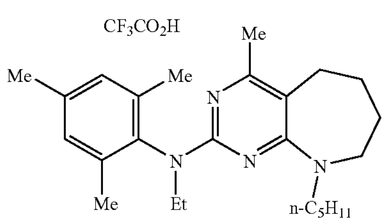 | Ethyl-(4-methyl-9-pentyl-6,7,8,9-tetrahydro-5H-pyrimido[4,5-b]azepin-2-yl)-(2,4,6-trimethyl-phenyl)-amine; compound with trifluoro-acetic acid | | 395.6 395 |

TABLE 3-continued

| cpd # | Structure | Name | mp (° C.) | [M + H]+ calc'd. observed |
|---|---|---|---|---|
| 136 | 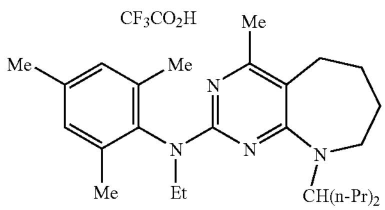 | Ethyl-[4-methyl-9-(1-propyl-butyl)-6,7,8,9-tetrahydro-5H-pyrimido[4,5-b]azepin-2-yl]-(2,4,6-trimethyl-phenyl)-amine; compound with trifluoro-acetic acid | | 423.7 423 |
| 137 | 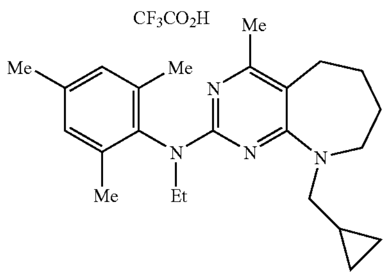 | (9-Cyclopropylmethyl-4-methyl-6,7,8,9-tetrahydro-5H-pyrimido[4,5-b]azepin-2-yl)-ethyl-(2,4,6-trimethyl-phenyl)-amine; compound with trifluoro-acetic acid | | 379.6 379 |
| 138 | 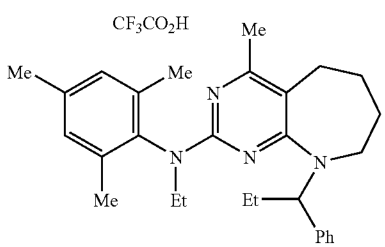 | Ethyl-[4-methyl-9-(1-phenyl-propyl)-6,7,8,9-tetrahydro-5H-pyrimido[4,5-b]azepin-2-yl]-(2,4,6-trimethyl-phenyl)-amine; compound with trifluoro-acetic acid | | 443.6 443 |
| 139 | 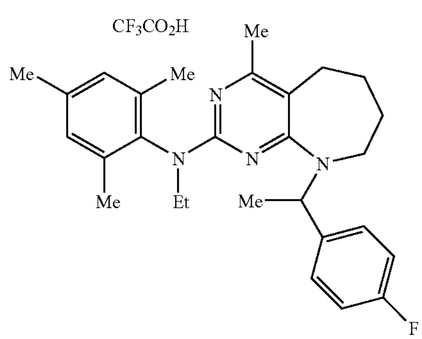 | Ethyl-{9-[1-(4-fluoro-phenyl)-ethyl]-4-methyl-6,7,8,9-tetrahydro-5H-pyrimido[4,5-b]azepin-2-yl}-(2,4,6-trimethyl-phenyl)-amine; compound with trifluoro-acetic acid | | 447.6 447 |
| 140 | 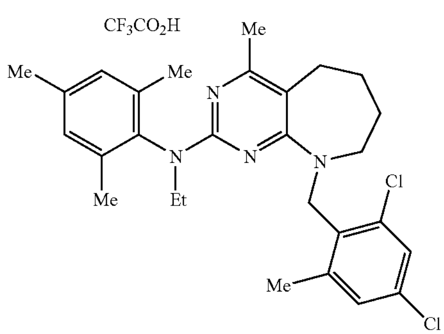 | [9-(2,4-Dichloro-6-methyl-benzyl)-4-methyl-6,7,8,9-tetrahydro-5H-pyrimido[4,5-b]azepin-2-yl]-ethyl-(2,4,6-trimethyl-phenyl)-amine; compound with trifluoro-acetic acid | | 497.5 497 |

TABLE 3-continued

| cpd # | Structure | Name | mp (° C.) | [M + H]+ calc'd. observed |
|---|---|---|---|---|
| 141 | 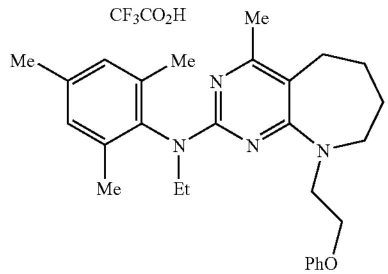 | Ethyl-[4-methyl-9-(2-phenoxy-ethyl)-6,7,8,9-tetrahydro-5H-pyrimido[4,5-b]azepin-2-yl]-(2,4,6-trimethyl-phenyl)-amine; compound with trifluoro-acetic acid | | 445.6 445 |
| 142 | 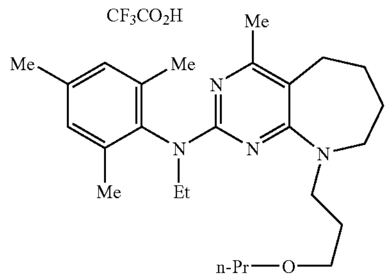 | Ethyl-[4-methyl-9-(3-propoxy-propyl)-6,7,8,9-tetrahydro-5H-pyrimido[4,5-b]azepin-2-yl]-(2,4,6-trimethyl-phenyl)-amine; compound with trifluoro-acetic acid | | 425.6 425 |
| 143 | 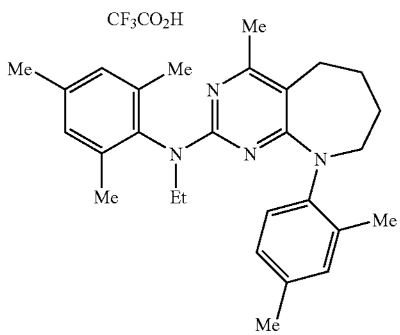 | [9-(2,4-Dimethyl-phenyl)-4-methyl-6,7,8,9-tetrahydro-5H-pyrimido[4,5-b]azepin-2-yl]-ethyl-(2,4,6-trimethyl-phenyl)-amine; compound with trifluoro-acetic acid | | 429.6 429 |
| 144 | 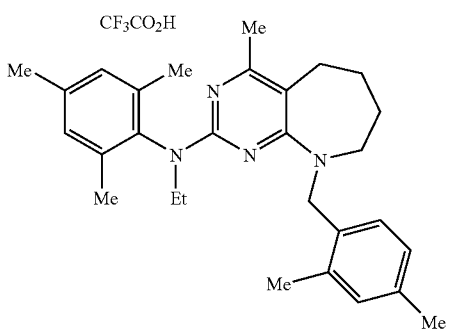 | [9-(2,4-Dimethyl-benzyl)-4-methyl-6,7,8,9-tetrahydro-5H-pyrimido[4,5-b]azepin-2-yl]-ethyl-(2,4,6-trimethyl-phenyl)-amine; compound with trifluoro-acetic acid | | 443.6 443 |
| 145 | 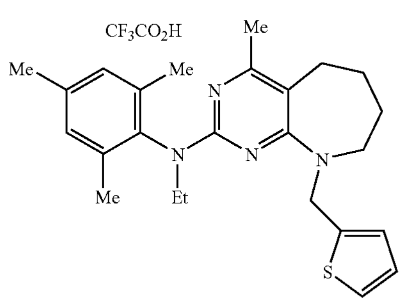 | (4-Methyl-9-thiophen-2-ylmethyl-6,7,8,9-tetrahydro-5H-pyrimido[4,5-b]azepin-2-yl)-(2,4,6-trimethyl-phenyl)-amine; compound with trifluoro-acetic acid | | 393.6 393 |

Dosage and Administration

The compounds of the present invention may be formulated in a wide variety of oral administration dosage forms and carriers. Oral administration can be in the form of tablets, coated tablets, dragees, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use.

Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The term "disease state" means any disease, condition, symptom, or indication. "Treating" or "treatment" of a disease state includes: (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms, or (iii) relieving the disease state, i.e., causing temporary or permanent regression of the disease state or its clinical symptoms.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical compositions in Example 8 are given to enable those skilled in the art to more clearly understand and to practice the present invention. They should not be considered as limiting the scope of the invention, but merely as being illustrative and representative thereof.

EXAMPLE 1

[4-Methyl-7-(1-propyl-butyl-6,7-dihydro-5H-pyrrolo [2,3-d]pyrimidin-2-yl]-(2,4,6-trimethyl-phenyl)-amine (37)

Step 1—N-(2,4,6-Trimethyl-phenyl)-guanidine; hydrochloride (IV).

A solution of 2,4,6-trimethyl-phenylamine (13.5 g, 100 mmol) in diethyl ether (50 mL) was added to a vigorously stirred solution of hydrogen chloride in diethyl ether (1.0 M, 100 mL, 100 mmol) at 0° C., followed by stirring at room temperature for 30 minutes. Removal of the solvent under reduced pressure afforded 2,4,6-trimethyl-phenylamine hydrochloride as an off-white solid (17.2 g, 100%), which was suspended in ethanol (100 mL) and treated with cyanamide (5.0 g, 120 mmol). The resulting solution was heated to reflux for 43 hours and then concentrated under reduced pressure. The viscous residue so obtained was triturated with diethyl ether (2×100 mL) to afford the guanidine hydrochloride IV as an hygroscopic, light brown foam (22 g, 100%; ESIMS m/z (M+H)=178).

Step 2—5-(2-Hydroxy-ethyl)-2-(2,4,6-trimethyl-phenylamino)-pyrimidin-4-ol (V).

A solution of N-(2,4,6-trimethyl-phenyl)-guanidine hydrochloride (17 g, 80 mmol) in ethanol (100 mL) was treated with sodium methoxide (4.3 g, 80 mmol) in methanol (18 mL), followed by 3-acetyl-dihydro-furan-2-one (2-acetylbutyrolactone, 10.3 g, 80 mmol). The reaction mixture was heated to reflux for 19 hours and then concentrated under reduced pressure. The residue so obtained was suspended in water (200 mL), and the resulting mixture was adjusted to pH 5 by the careful addition of concentrated hydrochloric acid, saturated with sodium chloride, and extracted with chloroform (3×500 mL). The combined extracts were dried over sodium sulfate, filtered, and concentrated under reduced pressure. The crude orange syrup so obtained was chromatographed over silica gel, eluting with a gradient of 0 to 10% methanol in dichloromethane, to afford the pyrimidinol V as a white powder (7.5 g, 38%; ESIMS m/z (M+H)=288).

Step 3—[4-Chloro-5-(2-chloro-ethyl)-pyrimidin-2-yl]-(2,4, 6-trimethyl-phenyl)-amine (VI).

To a vigorously stirred suspension of 5-(2-hydroxy-ethyl)-2-(2,4,6-trimethyl-phenylamino)-pyrimidin-4-ol (V; 4.6 g, 16 mmol) in toluene (100 mL) was added a solution of thionyl chloride (2.0 g, 17 mmol) in toluene (60 mL) over 30 minutes. The reaction mixture was stirred at room temperature for 69 hours and then concentrated under reduced pressure. The tan solid so obtained was dissolved in phosphorus oxychloride (49 g, 320 mmol) and heated to reflux for 19 hours. After cooling to room temperature, the reaction mixture was poured onto ice (500 g), neutralized with sodium hydrogen carbonate, and extracted with ethyl acetate (3×500 mL). The combined extracts were dried over magnesium sulfate, filtered, and concentrated under reduced pressure. The crude brown solid was chromatographed over silica gel, eluting with a gradient of 10 to 30% ethyl acetate in hexane, to afford the chloropyrimidine VI as a pale yellow solid (3.8 g, 92%; ESIMS m/z (M+H) 324).

Step 4—[4-Methyl-7-(1-propyl-butyl)-6,7-dihydro-5H-pyrrolo[2,3-d]pyrimidin-2-yl]-(2,4,6-trimethyl-phenyl)-amine (VII).

A solution of [4-chloro-5-(2-chloro-ethyl)-pyrimidin-2-yl]-(2,4,6-trimethyl-phenyl)-amine (1.3 g, 4.1 mmol) in N-methylpyrrolidinone (15 mL) was treated with 1-propyl-butylamine (1.6 g, 14 mmol) and heated to 120° C. in a sealed tube for 18 hours. Additional 1-ethyl-butylamine (0.76 g, 6.6 mmol) was added, and heating at 120° C. was resumed for 32 hours. The reaction mixture was concentrated under reduced pressure and the resulting orange solid was partitioned between ethyl acetate (100 mL) and water (100 mL). The aqueous layer was further extracted with ethyl acetate (2×75 mL), and the combined extracts were washed with 15% aqueous sodium hydroxide (2×50 mL) and brine (30 mL), dried over magnesium sulfate, filtered, and concentrated under reduced pressure. The crude brown oil was chromatographed over silica gel, eluting with a gradient of 1 to 15% methanol in dichloromethane, to provide VII as an off-white solid (0.64 g, 41%; ESIMS m/z (M+H)=367).

Step 5—Ethyl-[4-methyl-7-(1-propyl-butyl)-6,7-dihydro-5H-pyrrolo[2,3-d]pyrimidin-2-yl]-(2,4,6-trimethyl-phenyl)-amine; compound with trifluoro-acetic acid (VIII)

[4-Methyl-7-(1-propyl-butyl)-6,7-dihydro-5H-pyrrolo[2, 3-d]pyrimidin-2-yl]-(2,4,6-trimethyl-phenyl)-amine (0.040 g, 0.11 mmol) was treated with a fine suspension of sodium hydride in N,N-dimethylformamide (0.16 M, 1.0 mL, 0.16 mmol) under nitrogen. After 45 minutes shaking at room temperature, iodoethane (0.025 g, 0.16 mmol) was added, and the resulting mixture was shaken at room temperature for 8 hours, followed by 12 hours at 40° C. The reaction mixture was then treated with trifluoroacetic acid (1 drop) and concentrated under reduced pressure. The residue was purified by preparative, reversed-phase HPLC, eluting with 0.1% trifluoroacetic acid/water/acetonitrile, to afford 37 (ESIMS m/z (M+H)=395).

EXAMPLE 2

2-(2-Bromo-4-isopropyl-phenylamino)-8-(1-ethyl-propyl)-4-methyl-5,8-dihydro-6H-pyrido[2,3-d]pyrimidin-7-one (113)

Step 1—N-(2-Bromo-4-isopropyl-phenyl)-guanidine; hydrochloride (X).

To a solution of 2-bromo-4-isopropyl-phenylamine (IX; 17 g, 79 mmol) in ethanol (200 mL), cooled in an ice-water bath, was added gaseous hydrogen chloride over the course of 10 minutes followed by stirring at room temperature for 30 minutes. The reaction mixture was then concentrated under reduced pressure to afford 2-bromo-4-isopropyl-phenylamine; hydrochloride as a white solid (19.9 g, 100%), which was dissolved in warm ethanol (100 mL) and added to cyanamid (4.0 g, 95 mmol). The resulting solution was heated to reflux for 16 hours, with additional cyanamide (1.0 g, 24 mmol) being added after 4 h. The reaction mixture was then concentrated under reduced pressure, and the residue so obtained was triturated with diethyl ether (4×50 mL) to afford the guanidine hydrochloride as a tan semisolid (X; 21 g, 89%; ESIMS m/z (M+H)=256).

Step 2—3-[2-(2-Bromo-4-isopropyl-phenylamino)-4-hydroxy-6-methyl-pyrimidin-5-yl]-propionic acid ethyl ester (XI).

To a solution of N-(2-bromo-4-isopropyl-phenyl)-guanidine; hydrochloride (X; 21 g, 72 mmol) and 2-acetyl-pentanedioic acid diethyl ester (diethyl 2-acetylglutarate, 18 g, 79 mmol) in ethanol (100 mL) was added a solution of freshly prepared sodium ethoxide (87 mmol) in ethanol (50 mL). The reaction mixture was heated to reflux for 24 hours and then concentrated under reduced pressure. The residue so obtained was suspended in water (200 mL), and the resulting mixture was adjusted to pH 5 by the careful addition of concentrated hydrochloric acid, saturated with sodium chloride, and extracted with ethyl acetate (3×100 mL). The combined extracts were washed with brine (150 mL), dried over magnesium sulfate, filtered, and concentrated under reduced pressure. The crude, brown oil so obtained was chromatographed over silica gel, eluting with a gradient of 0.5 to 6% methanol in dichloromethane, to afford the hydroxypyrimidine as a cream solid (XI; 7.2 g, 21%; ESIMS m/z (M+H)=422).

Step 3—3-[2-(2-Bromo-4-isopropyl-phenylamino)-4-chloro-6-methyl-pyrimidin-5-yl]-propionic acid ethyl ester (XII).

A solution of 3-[2-(2-bromo-4-isopropyl-phenylamino)-4-hydroxy-6-methyl-pyrimidin-5-yl]propionic acid ethyl ester (XI; 6.6 g, 16 mmol) in phosphorus oxychloride (14 g, 94 mmol) was heated to reflux for 2.5 hours. After cooling to room temperature, the reaction mixture was poured onto ice (150 g) and extracted with ethyl acetate (2×150 mL). The combined extracts were washed sequentially with brine (150 mL), saturated aqueous sodium bicarbonate (100 mL), and brine (100 mL), then dried over magnesium sulfate, filtered, and concentrated under reduced pressure. The crude dark oil was chromatographed over silica gel, eluting with a gradient of 0 to 20% ethyl acetate in hexane, to afford the chloropyrimidine as a light yellow oil (XII; 3.8 g, 54%; ESIMS m/z (M+H)=440).

Step 4 2-(2-Bromo-4-isopropyl-phenylamino)-8-(1-ethyl-propyl)-4-methyl-5,8-dihydro-6H-pyrido[2,3-d]pyrimidin-7-one (113).

A solution of 3-[2-(2-bromo-4-isopropyl-phenylamino)-4-chloro-6-methyl-pyrimidin-5-yl]-propionic acid ethyl ester (XII; 0.22 g, 0.50 mmol) in N-methylpyrrolidinone (2.5 mL) was treated with 1-ethyl-propylamine (0.22 g, 2.5 mmol) and heated to 130° C. in a sealed tube for 130 hours. The cooled reaction mixture was poured onto water (50 mL) and extracted with diethyl ether (3×50 mL). The combined extracts were washed with brine (50 mL), dried over magnesium sulfate, filtered, and concentrated under reduced pressure. The brown solid was chromatographed over silica gel, eluting with 20% ethyl acetate in hexane, to provide 113 as a white solid (0.11 g, 43%; mp 124-126° C.; ESIMS m/z (M+H) 445).

EXAMPLE 3

(2-Bromo-4-isopropyl-phenyl)-[8-(1-ethyl-propyl)-4-methyl-5 6,7,8-tetrahydro-pyrido[2,3-d]pyrimidin-2-yl]-amine (114)

A solution of 2-(2-bromo-4-isopropyl-phenylamino)-8-(1-ethyl-propyl)-4-methyl-5,8-dihydro-6H-pyrido[2,3-d]pyrimidin-7-one (XIII; 0.070 g, 0.16 mmol) in tetrahydrofuran (1 mL) was cooled to 0° C. under nitrogen and treated with a solution of borane-tetrahydrofuran complex in tetrahydrofuran (1.0 M, 0.48 mL, 0.48 mmol). The reaction mixture was kept at room temperature for 20 hours, after which time solution of 33% acetic acid in ethyl acetate (1 mL) was added. The resulting mixture was allowed to stand at room temperature overnight, added to 3% aqueous sodium hydroxide (50 mL), and extracted with ethyl acetate (3×35 mL). The combined extracts were washed with 15% aqueous sodium hydroxide (15 mL) and brine (15 mL), dried over magnesium sulfate, filtered, and concentrated under reduced pressure to afford 114 as a clear, colorless film (0.066 g, 96%; ESIMS m/z (M+H)=431).

EXAMPLE 4

(2-Bromo-4-isopropyl-phenyl)-ethyl-[8-(1-ethyl-propyl)-4-methyl-5,6,7,8-tetrahydro-pyrido[2,3-d]pyrimidin-2-yl]-amine (116)

To a vigorously stirred suspension of sodium hydride (0.004 g, 0.17 mmol) in N,N-dimethylformamide (0.5 mL) under nitrogen was added a solution of (2-bromo-4-isopropyl-phenyl)-[8-(1-ethyl-propyl)-4-methyl-5,6,7,8-tetrahydro-pyrido[2,3-d]pyrimidin-2-yl]-amine (XIV; 0.056 g, 0.13 mmol) in N,N-dimethylformamide (0.5 mL). After 30 minutes at room temperature, iodoethane (0.026 g, 0.17 mmol) was added, and the resulting mixture was stirred at room temperature for 14 hours. The reaction mixture was then poured onto water (20 mL) and extracted with ethyl acetate (3×20 mL). The combined extracts were washed with brine (10 mL), dried over magnesium sulfate, filtered, and concentrated under reduced pressure. The yellow oil so obtained was chromatographed over silica gel, eluting with a gradient of 20 to 50% ethyl acetate in hexane, to afford 116 as a pale yellow oil (0.040 g, 67%). ESIMS m/z 459 (M+H).

EXAMPLE 5

Ethyl-(4-methyl-9-thiophen-2-ylmethyl-6,7,8,9-tetrahydro-5H-pyrimido[4,5-b]azepin-2-yl)-(2,4,6-trimethyl-phenyl)-amine; compound with trifluoro-acetic acid (123)

Step 1—3-Acetyl-oxepan-2-one (XVII).

To a solution of diisopropylamine (2.2 g, 22 mmol) in tetrahydrofuran (100 mL) at −78° C. was added a solution of butyllithium in hexanes (1.6 M, 14 mL, 22 mmol), under nitrogen. The resulting solution was stirred at −78° C. for 45 min and then treated with oxepan-2-one (XVI, 2.3 g, 20 mmol) in tetrahydrofuran (50 mL) over 15 minutes. The resulting solution was stirred at −78° C. for 1 hour and then treated with pyruvonitrile (1.5 g, 22 mmol). The resulting solution was stirred at −78° C. for 10 minutes and then treated with water (0.4 mL). The mixture was then poured onto diethyl ether (400 mL) and water (400 mL). The water layer was further extracted with diethyl ether (450 mL). The combined extracts were washed with brine (50 mL), dried over magnesium sulfate, filtered, and concentrated under reduced pressure. The resulting yellow oil was chromatographed over silica gel, eluting with a gradient of 5 to 30% ethyl acetate in hexane, to afford the ketoester as a colorless solid (XVII; 1.5 g, 48%; mp 53-59° C.).

Step 2—5-(4-Hydroxy-butyl)-6-methyl-2-(2,4,6-trimethylphenylamino)-pyrimidin-4-ol A solution of N-(2,4,6-trimethyl-phenyl)-guanidine; hydrochloride (IV; 2.0 g, 9.4 mmol) in ethanol (10 mL) was treated with sodium methoxide (0.52 g, 9.5 mmol) in methanol (2.2 mL), followed by 3-acetyl-oxepan-2-one (1.3 g, 8.2 mmol) in ethanol (2 mL). The reaction mixture was heated to reflux for 21 hours and then concentrated under reduced pressure. The residue so obtained was suspended in water (200 mL), and the resulting mixture was adjusted to pH 4 by the careful addition of concentrated hydrochloric acid and extracted with chloroform (2×50 mL). The combined extracts were dried over sodium sulfate, filtered, and concentrated under reduced pressure. The light brown solid so obtained was chromatographed over silica gel, eluting with a gradient of 1 to 7% methanol in dichloromethane, to afford the pyrimidinol as a white solid (XVIII; 1.2 g, 46%; ESIMS m/z (M+H)=316).

Step 3—[4-Chloro-5-(4-chloro-butyl)-6-methyl-pyrimidin-2-yl]-ethyl-(2,4,6-trimethyl-phenyl)-amine (XIX).

5-(4-Hydroxy-butyl)-6-methyl-2-(2,4,6-trimethyl-phenylamino)-pyrimidin-4-ol (1.0 g, 3.2 mmol) was dissolved in phosphorus oxychloride (12 g, 75 mmol) and heated to reflux for 17 hours. After cooling to room temperature, the reaction mixture was concentrated under reduced pressure. The residue so obtained was partitioned between aqueous sodium hydrogen carbonate (40 mL) and chloroform (50 mL), and the aqueous layer was further extracted with chloroform (25 mL). The combined extracts were washed with concentrated aqueous sodium hydrogen carbonate (25 mL) and brine (15 mL), dried over sodium carbonate, filtered, and concentrated under reduced pressure to afford the chloropyrimidine as a tan solid (XIX; 0.98 g, 84%; ESIMS (M+H) m/z 352). The product was used in the next step without purification.

Step 4—(4-Methyl-9-thiophen-2-ylmethyl-6,7,8,9-tetrahydro-5H-pyrimido[4,5-b]azepin-2-yl)-(2,4,6-trimethyl-phenyl)-amine (XX).

A solution of [4-chloro-5-(4-chloro-butyl)-6-methyl-pyrimidin-2-yl]-ethyl-(2,4,6-trimethyl-phenyl)-amine (XIX; 0.035 g, 0.10 mmol) in N-methylpyrrolidinone (0.4 mL) was treated with a solution of C-thiophen-2-yl-methylamine (2-thiophenemethylamine, 0.014 g, 0.125 mmol) in N-methylpyrrolidinone (0.125 mL) and triethylamine (0.025 g, 0.25 mmol) heated to 130 ° C. in a sealed tube for 65 hours. The reaction mixture was concentrated under reduced pressure and the residue so obtained was treated with sodium methoxide (0.011 g, 0.20 mmol) in methanol (0.4 mL). The resulting mixture was concentrated under reduced pressure to afford the tetrahydropyrimidoazepine XX as a dark solid together with sodium chloride. The product was used in the next step without further purification. Alternatively, the residue so obtained was purified by preparative, reversed-phase HPLC, eluting with 0.1% trifluoroacetic acid/water/ acetonitrile, to afford tetrahydropyrimidoazepine (XX; ESIMS m/z (M+H)=393).

Step 5—Ethyl-(4-methyl-9-thiophen-2-ylmethyl-6,7,8,9-tetrahydro-5H-pyrimido[4,5-b]azepin-2-yl)-(2,4,6-trimethyl-phenyl)-amine; compound with trifluoro-acetic acid (123).

(4-Methyl-9-thiophen-2-ylmethyl-6,7,8,9-tetrahydro-5H-pyrimido[4,5-b]azepin-2-yl)-(2,4,6-trimethyl-phenyl)-amine (XX; 0.039 g, 0.10 mmol) was treated with a fine suspension of sodium hydride in N,N-dimethylformamide (0.18 M, 1.0 mL, 0.18 mmol) under nitrogen. After 1.25 hours shaking at room temperature, iodoethane (0.028 g, 0.18 mmol) in N,N-dimethylformamide (0.15 mL) was added, and the resulting mixture was shaken at room temperature for 8 hours, followed by 9 hours at 40° C. The reaction mixture was then treated with trifluoroacetic acid (1 drop) and concentrated under reduced pressure. The residue so obtained was purified by preparative, reversed-phase HPLC, eluting with 0.1% trifluoroacetic acid/water/acetonitrile, to afford 123 (ESIMS m/z (M+H)=421).

EXAMPLE 6

CRF Receptor Binding Assay

Human IMR-32 neuroblastoma cells are grown to 80% confluence in MEM medium containing 10% heat-inactivated FBS, 1 mM sodium pyruvate, and 0.1 mM nonessential amino acids. Cell membranes are prepared according the method of Dieterich and DeSouza (1996). The cells (~5E+9) are resuspended in 10 volumes of wash buffer (5 mM Tris HCl, 10 mM $MgCl_2$, 2 mM EGTA, pH 7.4 at RT), homogenized with a Polytron, and then centrifuged at 45,000 G for 20 min at 4° C. The membrane pellets are washed twice with wash buffer (45,000 G for 20 min at 4° C.) and then resuspended (50 mM Tris HCl, 10 mM $MgCl_2$, 2 mM EGTA, pH 7.4 at RT). Protein concentration is determined using Pierce reagents and BSA as standard. Aliquots of 1-1.5 mL are stored at −80° C. until binding assay.

The competition binding assay is performed in a final volume of 250 µl, which contains assay buffer (50 mM Tris-HCl, 10 mM $MgCl_2$, 2 mM EGTA, 0.2% BSA, 0.1 mM bacitracin and 100 kIU/mL aprotinin pH 7.2 at R.T.), 0.05 nM [$^{125}$I]Tyr$^0$-ovine CRF (Du Pont New England Nuclear), 50 µg of membrane protein, and test compound at various concentrations. Non-specific binding is determined with 1 uM hCRF. Binding reactions are terminated after 2 hr incubation at 25° C. by filtering through 96-w GF/C filter plate using a Packard Harvester (Filtermate 196). The 96-w filter plate is pre-treated with 0.3% polyethyleneimine and pre-washed with washing buffer (50 mM Tris-HCl, 10 mM $MgCl_2$, 2 mM EGTA, 0.2% BSA, pH 7.2 at 4° C.). Unbound radioactivity is removed by four rapid washes (0.8 ml/well) with wash buffer. The radioactivity is quantified using a Packard TopCount. Data are analyzed using non-linear iterative curve fitting to obtain $IC_{50}$ and Hill slope values. $pK_i$ values are derived from $pIC_{50}$ values (−log of $IC_{50}$).

| Cpd | $pIC_{50}$ | $pK_i$ |
|-----|------------|--------|
| 2   | 5.68       | 6.71   |

EXAMPLE 7

Intracellular cAMP Stimulation Assay

Human Y-79 retinoblastoma cells are grown in RPMI 1640 medium with 15% FBS. Measures of cAMP accumulation are performed by using NEN Adenylyl Cyclase Flash-Plate kit (SMP004). The cells are separated from culture medium, washed twice with PBS (150 Xg, 8 min), resuspended (2E+6 cells/ml) in Stimulation Buffer (provided in the kit), and then added to 96-well FlashPlates, (50,000 cells per well). Various concentrations of test compounds are incubated with the cells for 20 min prior to the addition of hCRF (30 nM). The total assay volume is 100 μl. The assay is terminated after 20 mm after addition of the hCRF by addition of Detection Buffer and [$^{125}$I]cAMP. After 2 hr at room temperature the mixtures are aspirated and the bound radioactivity is measured with a Packard TopCount. The potency (IC$_{50}$ values) of test compounds in inhibiting the hCRF-stimulated accumulation of cAMP is determined by nonlinear regression analyses with interactive curve-fitting procedures.

EXAMPLE 8

Pharmaceutical compositions of the subject Compounds for administration via several routes were prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations (G)

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula I

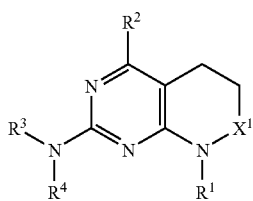

(I)

wherein, $X^1$ is $(CH_2)_n$ and n is zero;

$R^1$ is (i) $C_{1-10}$ alkyl optionally substituted with a substituent selected from the group consisting of amino, $C_{1-3}$ alkylamino, $C_{1-3}$ dialkylamino, ($C_{1-3}$ alkyl)arylamino and phenyl, said phenyl optionally substituted with (a) one to three substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl, (ii) $C_{3-7}$ cycloalkyl optionally substituted with $C_{1-3}$ alkyl, (iii) $C_{3-7}$ cycloalkyl-$C_{1-3}$ alkyl, (iv) benzofused-$C_{5-7}$ cycloalkyl, (v) phenyl or heteroaryl said phenyl and heteroaryl optionally substituted with one to three substituents independently selected from the group consisting of $C_{1-6}$ alkyl, $C_{1-4}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl;

(vi) heteroaryl-$C_{1-6}$alkyl said heteroaryl-$C_{1-6}$alkyl optionally substituted with one to three substituents selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl;

(vii) 1,2-diphenylethyl, (viii) $C_{1-3}$ alkoxy-$C_{1-6}$ alkyl, or, (ix) aryloxy-$C_{1-6}$ alkyl said aryloxy group being optionally substituted with one to three substituents selected form the group consisting of $C_{1-3}$ alkyl, $C_{1-3}$ alkoxy and halogen;

$R^2$ is $C_{1-6}$ alkyl or $C_{1-3}$ haloalkyl;

$R^3$ is (i) hydrogen, (ii) $C_{1-6}$ alkyl optionally substituted with hydroxy, $C_{1-3}$ alkoxy or $C_{1-3}$ acyloxy, (iii) $C_{3-6}$ alkenyl, (iv) $C_{3-7}$ cycloalkyl, (v) $C_{3-7}$ cycloalkyl-$C_{1-3}$ alkyl;

(vi) $C_{3-7}$ cycloalkenyl, (vii) $C_{3-7}$ cycloalkenyl-$C_{1-3}$ alkyl, (viii) benzyl optionally substituted with one to three groups independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl; and, $R^4$ is aryl optionally substituted with one to three groups independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl, and, individual isomers, racemic or non-racemic mixtures of isomers or pharmaceutically acceptable salts thereof.

2. A compound according to claim 1 wherein $R^1$ is (i) $C_{1-10}$ branched or unbranched alkyl; or, (ii) optionally substituted heteroaryl-$C_{1-6}$alkyl, said heteroaryl optionally substituted with a substituent selected from the group consisting of $C_{1-3}$ alkyl, $C_{1-3}$ alkoxy and halogen, (iii) optionally substituted phenyl or heteroaryl said phenyl or heteroaryl optionally substituted with a substituent selected from the group consisting of $C_{1-3}$ alkyl, $C_{1-3}$ alkoxy and halogen;

(iv) $C_{1-3}$ alkyl substituted with a phenyl said phenyl optionally substituted with a substituent selected from the group consisting of $C_{1-3}$ alkyl, $C_{1-3}$ alkoxy and halogen;

$R^3$ is (i) hydrogen, (ii) $C_{1-6}$ alkyl, (iii) $C_{3-7}$ cycloalkyl-$C_{1-3}$ alkyl, or, (iv) benzyl optionally substituted with $C_{1-3}$ alkyl, $C_{1-3}$ alkoxy or halogen;

$R^4$ is optionally substituted phenyl.

3. A compound according to claim 2 wherein $R^1$ is (i) $C_{1-10}$ branched or unbranched alkyl, (ii) $C_{1-3}$ alkyl substituted with a phenyl said phenyl optionally substituted, or (iii) heteroaryl-$C_{1-6}$ alkyl wherein said heteroaryl is 2-thienyl, 2-furanyl or 3-indolinyl each of said heteroaryl optionally substituted.

4. A compound according to claim 3 wherein $R^4$ is 2,4-disubstituted- or 2,4,6-trisubstituted-phenyl.

5. A method of treating a disease selected from the group consisting of phobias, stress-related illnesses, mood disorders, eating disorders, generalized anxiety disorders, stress-induced gastrointestinal dysfunctions, and neuropsychiatric disorders comprising administering to a patient in need thereof a therapeutically effective amount of a compound according to claim 1.

6. A pharmaceutical composition comprising a therapeutically effective amount of at least one compound of formula I (I)

wherein:
$X^1$ is $(CH_2)_n$;
n is 0;
$R^1$ is
  (i) $C_{1-10}$ alkyl optionally substituted with a substituent selected from the group consisting of amino, $C_{1-3}$ alkylamino, $C_{1-3}$ dialkylamino, ($C_{1-3}$ alkyl)arylamino and phenyl, said phenyl optionally substituted with (a) one to three substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^aR^b$, where $R^a$ and $R^b$ are each independently selected from the group consisting of hydrogen, $C_{1-6}$ alkyl, and $C_{1-6}$ alkylcarbonyl,
  (ii) $C_{3-7}$ cycloalkyl optionally substituted with $C_{1-3}$ alkyl,
  (iii) $C_{3-7}$ cycloalkyl-$C_{1-3}$ alkyl,
  (iv) benzofused-$C_{5-7}$ cycloalkyl,
  (v) phenyl or heteroaryl said phenyl and heteroaryl optionally substituted with one to three substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^aR^b$, where $R^a$ and $R^b$ are each independently selected from the group consisting of hydrogen, $C_{1-6}$ alkyl, and $C_{1-6}$ alkylcarbonyl;
  (vi) heteroaryl-$C_{1-6}$alkyl said heteroaryl-$C_{1-6}$alkyl optionally substituted with one to three substituents selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^aR^b$, where $R^a$ and $R^b$ are each independently selected from the group consisting of hydrogen, $C_{1-6}$ alkyl, and $C_{1-6}$ alkylcarbonyl;
  (vii) 1,2-diphenylethyl,
  (viii) $C_{1-3}$ alkoxy-$C_{1-6}$ alkyl, or,
  (ix) aryloxy-$C_{1-6}$ alkyl said aryloxy group being optionally substituted with one to three substituents selected form the group consisting of $C_{1-3}$ alkyl, $C_{1-3}$ alkoxy and halogen;

$R^2$ is $C_{1-6}$ alkyl or $C_{1-3}$ haloalkyl;
$R^3$ (i) hydrogen,
  (ii) $C_{1-6}$ alkyl optionally substituted with hydroxy, $C_{1-3}$ alkoxy or $C_{1-3}$ acyloxy,
  (iii) $C_{3-6}$ alkenyl,
  (iv) $C_{3-7}$ cycloalkyl,
  (v) $C_{3-7}$ cycloalkyl-$C_{1-3}$ alkyl;
  (vi) $C_{37}$ cycloalkenyl,
  (vii) $C_{3-7}$ cycloalkenyl-$C_{1-3}$ alkyl,
  (viii) benzyl optionally substituted with one to three groups independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^aR^b$, where $R^a$ and $R^b$ are each independently selected from the group consisting of hydrogen, $C_{1-6}$ alkyl, and $C_{1-6}$ alkylcarbonyl; and,
$R^4$ is aryl optionally substituted with one to three groups independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^aR^b$, where $R^a$ and $R^b$ are each independently selected from the group consisting of hydrogen, $C_{1-6}$ alkyl, and $C_{1-6}$ alkylcarbonyl; and
individual isomers, racemic or non-racemic mixtures of isomers, or pharmaceutically acceptable salts thereof, in admixture with at least one pharmaceutically acceptable carrier, diluent or excipient.

7. A process for the preparation of a compound according to formula I (I)

wherein,
$X^1$ is $(CH_2)_n$;
n is 0;
$R^1$ is
  (i) $C_{1-10}$ alkyl optionally substituted with a substituent selected from the group consisting of amino, $C_{1-3}$ alkylamino, $C_{1-3}$ dialkylamino, ($C_{1-3}$ alkyl)arylamino and phenyl, said phenyl optionally substituted with (a) one to three substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^aR^b$, where $R^a$ and $R^b$ are each independently selected from the group consisting of hydrogen, $C_{1-6}$ alkyl, and $C_{1-6}$ alkylcarbonyl,
  (ii) $C_{3-7}$ cycloalkyl optionally substituted with $C_{1-3}$ alkyl,
  (iii) $C_{37}$ cycloalkyl-$C_{1-3}$ alkyl,
  (iv) benzofused-$C_{5-7}$ cycloalkyl,
  (v) phenyl or heteroaryl said phenyl and heteroaryl optionally substituted with one to three substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl;

(vi) heteroaryl-$C_{1-6}$alkyl said heteroaryl-$C_{1-6}$alkyl optionally substituted with one to three substituents selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl;

(vii) 1,2-diphenylethyl, (viii) $C_{1-3}$ alkoxy-$C_{1-6}$ alkyl, or, (ix) aryloxy-$C_{1-6}$ alkyl said aryloxy group being optionally substituted with one to three substituents selected form the group consisting of $C_{1-3}$ alkyl, $C_{1-3}$ alkoxy and halogen;

$R^2$ is $C_{1-6}$ alkyl or $C_{1-3}$ haloalkyl;

$R^3$ is hydrogen;

$R^4$ is aryl optionally substituted with one to three groups independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl; and individual isomers, racemic or non-racemic mixtures of isomers, or pharmaceutically acceptable salts thereof comprising the steps of:

(i) contacting an aryl amine hydrochloride XXII wherein $R^4$ is as defined above with cyanamide to afford an aryl guanidinium hydrochloride XXIII;

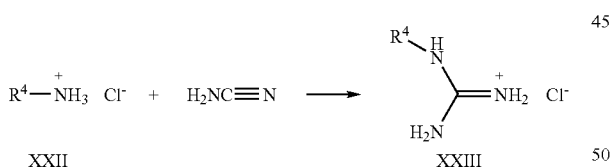

(ii) contacting said guanidine hydrochloride XXIII with a α-substituted β-keto ester XXIV wherein $R^2$ is $C_{1-6}$ alkyl and $R^6$ and $R^7$ together are $(CH_2)_o$ and o is 2 in the presence of base to afford the pyrimidine XXV wherein $R^5$ is $(CH_2)_2OH$;

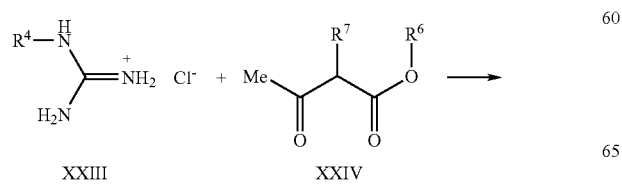

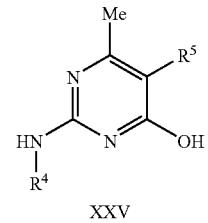

(iii) contacting said pyrimidine with a chlorinating agent sufficiently reactive to convert XXV to the corresponding chloropyrimidine XXVI and to convert a hydroxyalkylene side chain present at $R^5$ to the corresponding chloroalkylene substituent;

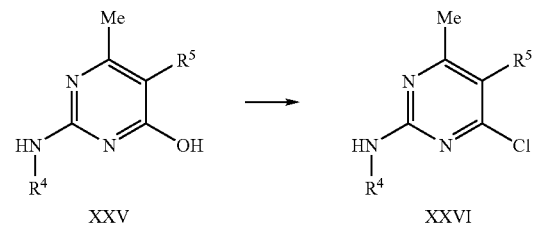

(iv) contacting said chloropyrimidine XXVI with a primary amine under conditions which displace the chlorine atoms on the pyrimidine and the $R^5$ side chain when $R^5$ is hydroxyalkylene resulting in the formation of the fused heterocyclic ring XXVII wherein X1 is absent

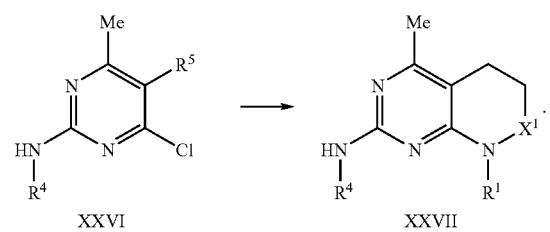

8. A process according to claim 7 further comprising contacting pyrimidine XXVII with base and an alkylating agent to afford the tertiary amine XXVIII:

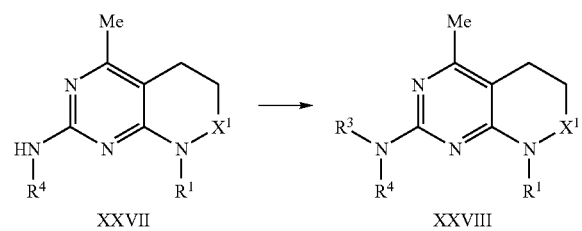

wherein
$R^3$ is
(i) $C_{1-6}$ alkyl optionally substituted with hydroxy, $C_{1-3}$ alkoxy or $C_{1-3}$ acyloxy,
(ii) $C_{3-6}$ alkenyl, (iii) $C_{3-7}$ cycloalkyl,
(iv) $C_{3-7}$ cycloalkyl-$C_{1-3}$ alkyl;
(v) $C_{3-7}$ cycloalkenyl,
(vi) $C_{3-7}$ cycloalkenyl-$C_{1-3}$ alkyl,
(vii) benzyl optionally substituted with one to three groups independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^aR^b$, where $R^a$ and $R^b$ are each independently selected from the group consisting of hydrogen, $C_{1-6}$ alkyl, and $C_{1-6}$ alkylcarbonyl.

* * * * *